US012371510B2

(12) United States Patent
Winter

(10) Patent No.: US 12,371,510 B2
(45) Date of Patent: Jul. 29, 2025

(54) PROCESS FOR CONCENTRATION OF ANTIBODIES AND THERAPEUTIC PRODUCTS THEREOF

(71) Applicants: Genentech, Inc., South San Francisco, CA (US); Novartis AG, Basel (CH)

(72) Inventor: Charles M. Winter, Belmont, CA (US)

(73) Assignees: Genentech, Inc., South San Francisco, CA (US); Novartis AG, Basel (CH)

( * ) Notice: Subject to any disclaimer, the term of this patent is extended or adjusted under 35 U.S.C. 154(b) by 665 days.

(21) Appl. No.: 17/017,465

(22) Filed: Sep. 10, 2020

(65) Prior Publication Data

US 2021/0095050 A1    Apr. 1, 2021

Related U.S. Application Data

(63) Continuation of application No. 16/752,366, filed on Jan. 24, 2020, now abandoned, which is a continuation of application No. 16/447,800, filed on Jun. 20, 2019, now abandoned, which is a continuation of application No. 14/257,907, filed on Apr. 21, 2014, now Pat. No. 10,370,456, which is a continuation of application No. 11/220,362, filed on Sep. 6, 2005, now abandoned.

(60) Provisional application No. 60/609,092, filed on Sep. 9, 2004.

(51) Int. Cl.
*A61K 39/395* (2006.01)
*B01D 61/14* (2006.01)
*B01D 61/16* (2006.01)
*C07K 1/34* (2006.01)
*C07K 16/06* (2006.01)
*C07K 16/42* (2006.01)

(52) U.S. Cl.
CPC .... *C07K 16/4291* (2013.01); *A61K 39/39591* (2013.01); *B01D 61/146* (2022.08); *B01D 61/16* (2013.01); *C07K 1/34* (2013.01); *C07K 16/065* (2013.01); *B01D 2311/04* (2013.01); *B01D 2311/16* (2013.01); *C07K 2317/21* (2013.01)

(58) Field of Classification Search
None
See application file for complete search history.

(56) References Cited

U.S. PATENT DOCUMENTS

| | | |
|---|---|---|
| 4,374,763 A | 2/1983 | Takagi |
| 4,485,040 A | 11/1984 | Roger |
| 4,576,696 A | 3/1986 | Oertli |
| 4,849,508 A | 7/1989 | Magnin |
| 4,897,465 A | 1/1990 | Cordle |
| 5,177,194 A | 1/1993 | Sarno |
| 5,252,480 A | 10/1993 | Yokota et al. |
| 5,256,294 A | 10/1993 | Van Reis |
| 5,580,856 A | 12/1996 | Prestrelski et al. |
| 6,103,502 A | 8/2000 | Moeller |
| 6,172,213 B1 | 1/2001 | Lowman |
| 6,252,055 B1 | 6/2001 | Relton |
| 6,875,432 B2 | 4/2005 | Shire |
| 8,961,964 B2 | 2/2015 | Liu et al. |
| 10,034,940 B2 | 7/2018 | Liu et al. |
| 10,370,456 B2 | 8/2019 | Winter |
| 11,767,370 B2 | 9/2023 | Winter |
| 2002/0045571 A1 | 4/2002 | Liu et al. |
| 2002/0151688 A1 | 10/2002 | Ristol |
| 2003/0190316 A1 | 10/2003 | Kakuta |
| 2004/0167320 A1 | 8/2004 | Couto |
| 2006/0051347 A1 | 3/2006 | Winter |
| 2007/0237762 A1 | 10/2007 | Winter |
| 2009/0214522 A1 | 8/2009 | Winter |
| 2014/0370003 A1 | 12/2014 | Winter |

FOREIGN PATENT DOCUMENTS

| | | |
|---|---|---|
| AU | 2005285243 B2 | 3/2012 |
| CN | 1219882 A | 6/1999 |
| EP | 0025275 A2 | 3/1981 |
| EP | 0210039 A2 | 1/1987 |
| EP | 0210039 A3 | 7/1988 |
| EP | 0467482 B1 | 1/1992 |
| EP | 0210039 B1 | 1/1993 |
| EP | 0787497 A2 | 8/1997 |
| EP | 0909564 A1 | 4/1999 |
| EP | 0822752 B1 | 2/2002 |
| EP | 1197221 A1 | 4/2002 |
| EP | 1780830 A1 | 5/2007 |
| EP | 2292636 A2 | 3/2011 |
| EP | 1610820 B2 | 8/2013 |
| EP | 1786830 B1 | 11/2014 |
| EP | 2335725 B1 | 10/2016 |
| EP | 2116265 B1 | 12/2020 |
| EP | 3805248 A2 | 4/2021 |

(Continued)

OTHER PUBLICATIONS

Anonymous (Jun. 2003). "Protein Concentration and Diafiltration by Tangential Flow Filtration," located at http://www.millipore.com/techpublications/tech1/tb032, last visited on Apr. 12, 2006, 20 pages.

Campbell, M.J. et al. (1993). "Effect of Temperature on Protein Conformation and Activity During Ultrafiltration," Journal of Membrane Science 78:35-43.

Communication Pursuant to Article 94(3) EPC, European Examination Report for European Patent Application No. 10 009 914.2, dated Nov. 5, 2018, filed on Sep. 20, 2010, 3 pages.

Genentech, Inc. (2008). "Process Characterization Summary Report," Genentech, Inc., 6 pages.

(Continued)

*Primary Examiner* — Yunsoo Kim
(74) *Attorney, Agent, or Firm* — Morrison & Foerster LLP

(57) ABSTRACT

The present disclosure provides a process for concentrating proteins including an ultrafiltering, a diafiltering, and a second ultrafiltering sequence, at elevated temperatures, such as above about 30° C. The disclosure also includes a process for preparing highly concentrated antibody compositions, and highly concentrated antibody products.

8 Claims, 17 Drawing Sheets

(56) References Cited

FOREIGN PATENT DOCUMENTS

| | | |
|---|---|---|
| EP | 4104859 A1 | 12/2022 |
| EP | 4108259 A1 | 12/2022 |
| EP | 3805248 B1 | 1/2023 |
| EP | 2292636 B9 | 1/2024 |
| EP | 4108259 B1 | 1/2024 |
| JP | S60214738 A | 10/1985 |
| JP | 6485929 A | 3/1989 |
| JP | H04198195 A | 2/1992 |
| JP | 05065295 A | 3/1993 |
| JP | H08205888 A | 8/1996 |
| JP | 9512267 A | 12/1997 |
| JP | 9512529 A | 12/1997 |
| JP | 2001516599 A | 10/2001 |
| RU | 2140287 C1 | 10/1999 |
| WO | 199006764 A1 | 6/1990 |
| WO | 199528951 A1 | 11/1995 |
| WO | 199528954 A1 | 11/1995 |
| WO | 199704801 A1 | 2/1997 |
| WO | 199726909 A1 | 7/1997 |
| WO | 199745140 A1 | 12/1997 |
| WO | 199915024 A1 | 4/1999 |
| WO | 200024266 A2 | 5/2000 |
| WO | 200024266 A3 | 7/2000 |
| WO | 200103515 A1 | 1/2001 |
| WO | 2001024814 A1 | 4/2001 |
| WO | 200213860 A1 | 2/2002 |
| WO | 0230463 A2 | 4/2002 |
| WO | 0230463 A3 | 10/2002 |
| WO | 2003009817 A2 | 2/2003 |
| WO | 2003039485 A2 | 5/2003 |
| WO | 2003042344 A2 | 5/2003 |
| WO | 2003072060 A2 | 9/2003 |
| WO | 2003042344 A3 | 11/2003 |
| WO | 2004001007 A2 | 12/2003 |
| WO | 2004042012 A2 | 5/2004 |
| WO | 2004001007 A3 | 7/2004 |
| WO | 2004055516 A1 | 7/2004 |
| WO | 2004076695 A1 | 9/2004 |
| WO | 2004091658 A1 | 10/2004 |
| WO | 2004042012 A3 | 11/2004 |
| WO | 2005073252 A1 | 8/2005 |
| WO | 2005082109 A2 | 9/2005 |
| WO | 2006031560 A2 | 3/2006 |
| WO | 2006031560 A3 | 8/2006 |

OTHER PUBLICATIONS

International Search Report dated Apr. 27, 2006, for PCT Application No. PCT/US2005/031844, filed on Sep. 8, 2005, 3 pages.
Lipnizki, F. et al. (2002). "Concepts of Industrial-Scale Diafiltration Systems," presented at the International Congress of membranes and Membrane Processes (ICOM), Toulouse, France, Desalination 144:179-184.
Liu, C. et al. (1998). "Optimization of Operation Parameters in Ultrafiltration Process," J. Biotechnology 66:195-202.
Sawada, K. et al. (1992). "Selective Removal of Anti-Acetylcholine Receptor Antibody in the Low Temperature Operation of Membrane Plasma Fractionation," J. Clin. Apher. 7(2):81-86. (Abstract Only).
Schwartz, L. (2003). "Diafiltration: A Fast, Efficient, Method for Desalting, or Buffer Exchange of Biological Samples," located at http://www.pall.com/pdf/02.0629_Buffer_Exchange_STR.pdf, last visited on Apr. 12, 2006, 6 pages.
Song, H-X. et al. (Feb. 2003). "Studies on Separation of IgY by Ultrafiltration," Journal of Shaanxi University of Science & Technology 21(1):44-46. (Chinese Language with certified English Translation, seven pages.).
U.S. Metric Association. (2012). "Metric System Temperature (Kelvin and Degree Celsius)," located at http://lamar.colostate.edu/~hillger/temps.htm, last visited on Jul. 7, 2014, 4 pages.
Van Den Berg, G.B. et al. (1990). "Flux Decline In Ultrafiltration Processes," Desalination 77:101-133.
Van Reis, R. et al. (1997). "Constant Cwall Untrafiltration Process Control," J. Membrane Science 130:123-140.
Vermeer, A.W.P. t al. (Jan. 2000). "The Thermal Stability of Immunoglobulin: Unfolding and Aggregation of a Multi-Domain Protein," Biophysical Journal 78(1):394-404.
Wagner, J. (Nov. 2001). Membrane Filtration Handbook Pratical Tips and Hints, Second Edition, Revision 2, pp. 1-127.
Winter, C.M. (Nov. 18, 2002). "High Concentration Formulation of RhuMAbs by Ultrafiltration," Biopharmaceutical Product Week, Abstract located at http://www.LifeSciencesInfo.com, last visited Oct. 30, 2002, 2 pages.
Written Opinion dated Apr. 27, 2006, for PCT Application No. PCT/US2005/031844, filed on Sep. 8, 2005, 5 pages.
Yao, H-J. et al. (Dec. 2003). "Operation Modes of Pressure-Driven Membrane Processes and Their Optimization," Membrane Science and Technology 23(6):38-43. (Chinese Language with certified English Translation, 13 pages.).
Zeman, L.J. et al. (1996). "Proces Configurations," Chapter 8 in Microfiltration and Ultrafiltration. Principles and Applications, Marcel Dekker, Inc., New York, New York, pp. 394-395.
Zydney, A.L. et al. (2000). "Protein Concentration and Buffer Exchange Using Ultrafiltration," Chapter 3 in Methods in Biotechnology, Desal, M.A., ed., Humana Press, Totowa, New Jersey, pp. 23-34.
Anonymous. (2002). "Omalizumab," Biodrugs 16:380-386.
Busse, W.W. (2002). "Anti-Immunoglobulin E (Omalizumab) Therapy in Allergic Asthma," Am J Respir Crit Care Med. 164:S12-S17.
Chen, B. et al. (2003). "Influence of Histidine on the Stability and Physical Properties of a Fully Human Antibody in Aqueous and Solid Forms," Pharm Res 20(12): 1952-1960.
Communication Pursuant to Article 94(3) EPC, dated Jan. 31, 2022, for European Patent Application No. 20200642.5, filed on Oct. 7, 2020, 6 pages.
European Search Report dated Jun. 10, 2021, for European Patent Application No. 20200642.5, 19 pages.
European Search Report dated Mar. 11, 2021, for European Patent Application No. 20200642.5, 15 pages.
World Health Organization. (2000). "Proposed INN: List 84," WHO Drug Information 14(4):263.
World Health Organization. (2001). "Recommended INN: List 46," WHO Drug Information 15(3-4):205.
Liu et al. (Sep. 2005). "Reversible Self-Association Increases the Viscosity of a Concentrated Monoclonal Antibody in Aqueous Solution," J. Pharm. Sci. 94(9): 1928-1940.
Daugherty, A. L. et al. (2006). "Formulation and Delivery Issues for Monoclonal Antibody Therapeutics, " Advanced Drug Delivery Reviews 58:686-706.
Nayar, R. et al. (2002) "Chapter 8 - High Throughput Formulation: Strategies for Rapid Development of Stable Protein Products," In Carpenter & Manning (eds.) Rational Design of Stable Protein Formulations, pp. 177-198.
Shiraki, K. et al. (2002). "Biophysical Effect of Amino Acids on the Prevention of Protein Aggregation," Biochem. 132:591-595.
Tomar, D.S. et al. (2017). "In-Silico Prediction of Concentration-Dependent Viscosity Curves for Monoclonal Antibody Solutions," MABS 9(3):476-489.
Tsumoto, K. et al. (2004). "Role of Arginine in Protein Refolding, Solubilization and Purification," Biotechnol. Prog. 20(5): 1301-1308.
U.S. Appl. No. 60/460,659, filed Apr. 4, 2003, 100 pages.
Wang, W. et al. (2007). "Antibody Structure, Instability, and Formulation," J. Pharm. Sci. 96(1):1-26.
Xie, Q. et al. (2004). "The Guanidine Like Effects of Arginine on Aminoacylase and salt-Induced Molten Globule State," Int. J. Biochem. Cell Biol. 36:296-306.
XOLAIR® (2003). FDA Label—"Omalizumab," 17 pages.
XOLAIR® (2005). "Scientific Discussion," European Public Assessment Report. 34 pages.
XOLAIR® (2023). "Summary of Product Characteristics," European Public Assessment Report. 182 pages.
Yadav, S. et al. (2011). "Establishing a Link Between Amino Acid Sequences and Self-Associating and Viscoelastic Behavior of Two Closely Related Monoclonal Antibodies," Pharm. Res. 28:1750-1764.

(56) References Cited

OTHER PUBLICATIONS

European Patent No. 1610820 B1 (EP Appln. No. 04759018.7) Supplementary data submitted by Proprietor with the letter dated, Sep. 9, 2012, 4 pages.
European Patent No. 1610820 B1 (EP Appln. No. 04759018.7) Decision of Opposition Division, Dec. 12, 2012, 16 pages.
European Patent No. 1786830 B1 (EP Appln. No. 05806393.4) Decision of Opposition Division, Nov. 16, 2017, 25 pages.
European Patent No. 2292636 B9 (EP Appln. No. 10009914.1) Decision of Technical Board of Appeal, May 5, 2022, 14 pages.
European Patent No. 3805248 B1 (Ep Appln. No. 20200642.5) Rule 58 EPC Communication, Oct. 28, 2020, 1 page.
European Patent No. 3805248 B1 (EP Appln. No. 20200642.5) Response to Rule 58 EPC Communication, Nov. 3, 2020, 8 pages.
European Patent No. 3805248 B1 (EP Appln. No. 20200642.5) European Search Report, May 31, 2021, 7 pages.
European Patent No. 3805248 B1 (EP Appln. No. 20200642.5) Search Opinion, Jun. 10, 2021, 10 pages.
European Patent No. 3805248 B1 (EP Appln. No. 20200642.5) Response to Search Opinion, Jul. 26, 2021, 23 pages.
European Patent No. 3805248 B1 (EP Appln. No. 20200642.5) Third Party Observations, Sep. 22, 2021, 3 pages.
European Patent No. 3805248 B1 (EP Appln. No. 20200642.5) Response to Third Party Observations, Oct. 4, 2021, 2 pages.
European Patent No. 3805248 B1 (EP Appln. No. 20200642.5) Examination Report, Jan. 31, 2022, 4 pages.
European Patent No. 3805248 B1 (EP Appln. No. 20200642.5) Response to Examination Report, Apr. 13, 2022, 6 pages.
European Patent No. 3805248 B1 (EP Appln. No. 20200642.5) Third Party Observations, May 24, 2022, 13 pages.
European Patent No. 3805248 B1 (EP Appln. No. 20200642.5) Third Party Observations, Aug. 23, 2022, 4 pages.
European Patent No. 3805248 B1 (EP Appln. No. 20200642.5) Intention to Grant, Dec. 2, 2022, 10 pages.
European Patent No. 3805248 B1 (EP Appln. No. 20200642.5) Communication of Further Notices of Opposition pursuant to Rule 79(2) EPC by Celltrion, Inc., Nov. 2, 2023, 51 pages.
European Patent No. 3805248 B1 (EP Appln. No. 20200642.5) Communication of Further Notices of Opposition pursuant to Rule 79(2) EPC by Kilburn & Strode LLP, Nov. 2, 2023, 33 pages.
European Patent No. 3805248 B1 (EP Appln. No. 20200642.5) Declaration of H.W. Frijlink, Jan. 11, 2024, 16 pages.
European Patent No. 3805248 B1 (EP Appln. No. 20200642.5) Response to Notices of Opposition, Mar. 4, 2024, 33 pages.
Ahn, J.H. et al. (1997). "Investigation of Refolding Condition for Pseudomonas fluorescens Lipase by Response Surface Methodology," Journal of Biotechnology 54:151-160.
Arakawa, T. et al. (2001). "Factors Affecting Short-Term and Long-Term Stabilities of Proteins," Advanced Drug Delivery Reviews 46:307-326.
Arakawa, T. et al. (2003). "Effects of Protein Stabilizers on Aggregation Inducted by Multiple-Stresses," The Yakugaku Zasshi 123(11):957-961.
Arakawa, T. et al. (2003). "The Effects of Arginine on Refolding of Aggregated Proteins: Not Facilitate Refolding, but Suppress Aggregation," Biochemical and Biophysical Communication 304:148-152.
Arakawa, T. et al. (2004, e-pub. May 20, 2004). "Elution of Antibodies From a Protein-A col. by Aqueous Arginine Solutions," Protein Expression and Purification 36:244-248.
Buchner, J. et al. (1992). "A Method for increasing the Yield of Properly Folded Recombinant Fusion Proteins: Single-Chain Immunotoxins from Renaturation of Bacterial Inclusion Bodies," Analytical Biochemistry 205(2):263-270.
Carpenter, J.F. et al. (1998). "Application of Infrared Spectroscopy to Development of Stable Lyophilized Protein Formulations," European Journal of Pharmaceutics and Biopharmaceutics 45:231-238.
Carpenter, J.F. et al. (1999). "Inhibition of Stress-Induced Aggregation of Protein Therapeutics," Methods in Enzymology 309:236-255.

Carpenter, J.F. et al. (2002). "Long-Term Storage of Proteins," in Current Protocols in Protein Science, John Wiley & Sons, Inc. Supplement 27, 4.6.1-4.6.6, 6 pages.
Carpenter, J.F. et al. (1997) "Rational Design of Stable Lyophilized Protein Formulations: Some Practical Advice," Pharmaceutical Research 14(8): 969-975.
Chang, B.S. et al. (2002). "Chapter 1: Practical Approaches to Protein Formulation Development," in Carpenter & Manning (eds.), Rational Design of Stable Protein Formulations, Kluwer Academic / Plenum Publishers, pp. 1-25.
Chi, E. et al. (2003) Physical Stability of Proteins in Aqueous Solution: Mechanism and Driving Forces in Nonnative Protein Aggregation, Pharmaceutical Research 20(9): 1325-1336.
Das, D. et al. (2004). "Development of a Biotin Mimic Tagged ScFv Antibody Against Western Equine Encephalitis Virus: Bacterial Expression and Refolding," Journal of Virological Methods 117:169-177.
European Medicines Agency (Mar. 21, 2024). "Omalizumab, Summary of Opinion," 2 pages.
European Medicines Agency (Oct. 23, 2014). "Guidelines on Similar Biological Medicinal Products," 7 pages.
European Patent No. 3805248 B1 (EP Appln. No. 20200642.5) Declaration and CV of H.W. Frijlink, filed in Writ of Summons dated Oct. 9, 2023, Celltrion Inc. & Celltrion Healthcare B.V. v. Novartis AG & Genentech, Inc., District Court in The Hague, Netherlands, 52 pages.
European Patent No. 3805248 B1 (EP Appln. No. 20200642.5) Declaration of Professor Daan Crommelin, filed in Novartis AG and Genentech, Inc. vs Celltrion Inc., filed Apr. 8, 2024, in the Unified Patent Court (UPC), Court of First Instance, Dusseldorf, Germany, 10 pages.
European Patent No. 3805248 B1 (EP Appln. No. 20200642.5) Extract From Register of European Patents, retrieved Apr. 4, 2024, 8 pages.
European Patent No. 3805248 B1 (EP Appln. No. 20200642.5) Response to Third Party Observations, Jul. 18, 2022, 5 pages.
European Patent No. 3805248 B1 (EP Appln. No. 20200642.5) Technical Background on Histidine Chemistry, filed in Novartis AG and Genentech, Inc. vs Celltrion Inc., filed Apr. 8, 2024, in the Unified Patent Court (UPC), Court of First Instance, Dusseldorf, Germany, 6 pages.
Georgiou, G. et al. (1996). "Expression of Correctly Folded Proteins in Escherichia coli," Current Opinion in Biotechnology 7:190-197.
Horan, T.P. et al. (1997). "Dimerization of Granulocyte-Colony Stimulating Factor Receptor: The Ig Plus CRH Construct of Granulocyte-Colony Stimulating Factor Receptor Forms 2:2 Complex with a Ligand," J. Biochem. 121:370-375.
Hsu, C.C. et al. (1995). "Surface Denaturation of Solid-Void Interface - A Possible Pathway by Which Opalescent Particulates Form During the Storage of Lyophilized Tissue-Type Plasminogen Activator at High Temperatures," Pharmaceutical Research 12(1):69-77.
Manning, M.C. et al. (1995). "Approaches For Increasing the Solution Stability of Proteins," Biotechnology and Bioengineering 48:506-512.
Menzella, H.G. et al. (2002). "High Recovery of Prochymosin From Inclusion Bodies Using Controlled Air Oxidation," Protein Expression and Purification 25:248-255.
Nelson, D.L. & Cox, M.M. (2000). Lehninger Principles of Biochemistry, 3rd edition, Nelson & Cox (eds.), Worth Publishers, New York, NY, various extracts, 47 pages.
Oberg, K. et al. (1994). "Nativelike Secondary Structure in Interleukin-1B Inclusion Bodies by Attenuated Total Reflectance FTIR," Biochemistry 33(9): 2628-2634.
Rinas, U. et al. (1990). "Denaturation-Renaturation of the Fibrin-Stabilizing Factor XIII a-Chain Isolated from Human Placenta: Properties of the Native and Reconstituted Protein," Biol. Chem. Hoppe-Seyler 371:49-56.
Rudolph, R. et al. (1996). "In Vitro Folding of Inclusion Body Proteins," The FASEB Journal 10:50-56.
Schulze, E. et al. (1887). "Über das Arginin," Zeitschrift für Physiologische Chemie, 11(1-2):43-65. English translation by machine with original German reference, 46 pages.

(56) References Cited

OTHER PUBLICATIONS

Schaffner, J. et al. (2001). "Cosecretion of Chaperones and Low-Molecular-Size Medium Additives Increases the Yield of Recombinant Disulfide-Bridged Proteins," Applied and Environmental Microbiology 67(9): 3994-4000.
Soejima, K. et al. (2001). "An Efficient Refolding Method for the Preparation of Recombinant Human Prethrombin-2 and Characterization f the Recombinant-Derived a-Thrombin," J. Biochem. 130:269-277.
Sörensen, S.P.L. (1910). "Über die Synthese des dl-Arginins (a-Amino-o-guanido-n-valeriansäure) und der isomeren a-Guanido-o-amino-n-valeriansäure," Berichte der deutschen chemischen Gesellschaft, 43(1):643-651. English translation by machine with original German reference, 18 pages.
Tsumoto, K. et al. (2003). "Practical Consideration in Refolding Proteins from Inclusion Bodies," Protein Expression and Purification 28:1-8.
Tsumoto, K. et al. (2003). "Solubilization of Active Green Fluorescent Protein from Insoluble Particles by Guanidine and Arginine," Biochemical and Biophysical Research Communication 312:1383-1386.
Turker, M. et al. (1987). "Membrane Fouling in a Constant-Flux Ultrafiltration Cell," Journal of Membrane Science 34:267-281.
Umetsu, M. et al. (Mar. 14, 2003). "How Additives Influence the Refolding of Immunoglobulin-Folded Proteins in a Stepwise Dialysis System," The Journal of Biological Chemistry 278(11): 8979-8987.
Urieto, J.O. et al. (2004). "Expression and Purification of the Recombinant Diphtheria Fusion Toxin DT388IL3 for Phase I Clinical Trials," Protein Expression and Purification 33: 123-133.
Wang, W. (1999). "Instability, Stabilization, and Formulation of Liquid Protein Pharmaceuticals," International Journal of Pharmaceutics 185:129-188.
Wang, W. (2000). "Lyophilization And Development Of Solid Protein Pharmaceuticals," International Journal Of Pharmaceutics 203:1-60.
Wang, W. (2005) "Protein Aggregation and its Inhibition in Biopharmaceutics," International Journal of Pharmaceutics 289:1-30.
Wang, Y.- C. J. et al. (1988). "Parenteral Formulations of Proteins and Peptides: Stability and Stabilizers," Journal of Parenteral Science and Technology, 46:S4-S24, 24 pages.
Wright, E. et al. (2004). "Isolation of Aminoglycoside Nucleotidyltransferase(2')'Ia from Inclusion Bodies as Active, Monomeric Enzyme," Protein Expression and Purification 35:373-380.
XOLAIR® (2021) U.S. Prescribing Information, 52 pages.
XOLAIR® (2022) Safety Data Sheet, 22 pages.
Zbacnik, T.J. et al. (2017, e-pub. Nov. 26, 2016). "Role of Buffers in Protein Formulations," Journal of Pharmaceutical Sciences 106:713-733.
European Patent No. 3805248 B1 (EP Appln. No. 20200642.5) Technical Background, filed in Writ of Summons dated Oct. 9, 2023, *Celltrion Inc. & Celltrion Healthcare B.V.* v. *Novartis AG & Genentech, Inc.*, District Court in The Hague, Netherlands, Original Dutch reference with English translation by machine, 27 pages.
Crommelin, D.J.A. et al. (2002). Pharmaceutical Biotechnology: Fundamentals and Applications, 2nd edition, Taylor & Francis, excerpt from Chapter 4, 74-75, 4 pages.
Dent, G. (2003). "IgE Modulation in Asthma," Expert Opin. Ther. Patents 13(10): 1607-1617.
PubMed (2024). Search for rhumAb E25 + Omalizumab + Xolair in years 2001-2004, 3 pages.
Cacia, J. et al. (1996). "Isomerization of an Aspartic Acid Residue in the Complementarity-Determining Regions of a Recombinant Antibody to Human IgE: Identification and Effect on Binding Affinity," Biochemistry 35(6): 1897-1903.
European Patent No. 1610820 B1 (EP AppIn No. 04759018.7) Response to Notice of Opposition, Jan. 24, 2012, 17 pages.
European Patent No. 2335725 B1 (EP Applin. No. 10008980.4) Response to Examination Report, Oct. 31, 2013, 3 pages.

European Patent No. 3805248 B1 (EP Appln. No. 20200642.5) Request for Acceleration of Opposition Proceeding, May 22, 2024, 73 pages.
Presta, L.G. et al. (Sep. 1, 1993). "Humanization of an Antibody Directed Against IgE," J. Immunol. 151 (5):2623-2632.
Ames, S.A. et al. (Mar. 2004). "Fresh From the Pipeline: Omalizumab," Nature Reviews Drug Discovery 3:199-200.
AVASTIN@ [Bevacizumab] (Feb. 2004). Package Insert, Genentech, Inc., South San Francisco, CA, 5 pages.
Ayres, J.G. et al. (2004). "Efficacy and Tolerability of Anti-Immunoglobulin E Therapy with Omalizumab in Patients with Poorly Controlled (Moderate-to-Severe) Allergic Asthma," Allergy 59:701-708.
Baynes, B.M. et al. (2004). "Rational Design of Solution Additives for the Prevention of Protein Aggregation," Biophysical Journal 87:1631-1639.
Baynes, B.M. et al. (2005). "Role of Arginine in the Stabilization of Proteins Against Aggregation," Biochemistry 44:4919-4925.
Beasley, R. (2004). "Examining the Unmet Need in Inadequately Controlled Severe Allergic Asthma," screen shot from The ERS International Congress 2004, Glasgow, website, 2 pages.
BEXXAR® [Tositumomab] (Jun. 2003). Package Insert, Corixa Corp., Seattle, WA and GlaxoSmithKline, Philadelphia, PA, 11 pages.
British Thoracic Society (Apr. 2004). "British Guideline on the Management of Asthma," 93 pages.
Buhl, R. et al. (2002). "Omalizumab Provides Long-Term Control in Patients with Moderate-to-Severe Allergic Asthma," Eur. Respir. J. 20:73-78.
Busse, W. et al. (2001). "Omalizumab, Anti-IgE Recombinant Humanized Monoclonal Antibody, for the Treatment of Severe Allergic Asthma," J. Allergy Clin. Immunol. 108(2): 184-190.
CAMPATH® [Alemtuzumab] (Apr. 2004). Package Insert, BERLEX® Laboratories, Montville, NJ, 4 pages.
Clayden et al. (2001). "Acidity, Basicity, and pKa," in Organic Chemistry 1st Edition, Outline, Contents and Chapter 8. pp. 181-208, 44 pages.
ERBITUX® [Cetuximab] (Jun. 2004). Package Insert, Bristol-Myers Squibb Company, Princeton, NJ, 3 pages.
European Medicines Agency and European Commission (2019). "Biosimilars in the EU: Information Guide for Healthcare Professionals," 40 pages.
European Patent No. 3805248 B1 (EP Appln. No. 20200642.5) Brief Communication of Acceleration of Opposition Proceedings, Jun. 17, 2024, 1 page.
European Patent No. 3805248 B1 (EP Appln. No. 20200642.5) Declaration and CV of Attorney J.B. Beeksma, filed in Deed Containing the Submission of Further Exhibits dated Aug. 7, 2024, *Novartis AG & Genentech, Inc.* v. *Celltrion Inc. & Celltrion Healthcare B.V.*, District Court in The Hague, Netherlands, Original Dutch reference with English translation, 9 pages.
European Patent No. 3805248 B1 (EP Appln. No. 20200642.5) Declaration and CV of Prof. D. Crommelin, filed in Deed Containing the Submission of Further Exhibits dated Aug. 7, 2024, *Novartis AG & Genentech, Inc.* v. *Celltrion Inc. & Celltrion Healthcare B.V.*, District Court in The Hague, Netherlands, Original Dutch reference with English translation, 35 pages.
European Patent No. 3805248 B1 (EP Appln. No. 20200642.5) Expert Declaration and Annex of Prof. Frijlink dated Jun. 26, 2024, filed by Celltrion, Inc. in Opposition Proceedings on Jul. 3, 2024, 19 pages.
European Patent No. 3805248 B1 (EP Appln. No. 20200642.5) Expert Declaration and CV of Prof. T. Dingermann dated Jun. 26, 2004, filed by Celltrion, Inc. in Opposition Proceedings on Jul. 3, 2024, 17 pages.
European Patent No. 3805248 B1 (EP Appln. No. 20200642.5) Expert Declaration and Resume of Dr. de Leede dated Jun. 26, 2024, filed by Celltrion, Inc. in Opposition Proceedings on Jul. 3, 2024, 27 pages.
European Patent No. 3805248 B1 (EP Appln. No. 20200642.5). Response to O1's Submission, filed by Genentech, Inc. and Novartis AG in Oral Proceedings on Jun. 11, 2024, 10 pages.

(56) References Cited

OTHER PUBLICATIONS

FDA (Jul. 2, 2024). "Biological Product Definitions," U.S. Food & Drug Administration, 2 pages.

Frokjaer, S. et al. (2000). Except from "Peptides and Proteins as Parental Solutions" in Pharmaceutical Formulation Development of Peptides and Proteins, pp. 150-153, 6 pages.

Genentech, Inc. (Jun. 30, 2004). U.S. Securities and Exchange Commission, Form 10-Q, 48 pages.

Giancola, C. et al. (1997). "DSC Studies on Bovine Serum Albumin Denaturation Effects of Ionic Strength and SDS Concentration," International Journal of Biological Macromolecules 20:193-204.

Global Initiative for Asthma (2004). "Global Strategy for Asthma Management and Prevention," 199 pages.

HERCEPTIN® [Trastuxumab] (Oct. 2003). Package Insert, Genentech, Inc., South San Francisco, CA, 5 pages.

Holgate, S.T. et al. (2004). "Efficacy and Safety of a Recombinant Anti-Immunoglobulin E Antibody (Omalizumab) in Severe Allergic Asthma," Clin. Exp. Allergy 34:632-638.

Humbert, M. et al. (2005). "Benefits of Omalizumab as Add-On Therapy in Patients with severe Persistent Asthma who are Inadequately Controlled Despite Best Available Therapy (GINA 2002 Step 4 Treatment): INNOVATE," Allergy 60:309-316.

HUMIRA® [Adalimumab] (Jul. 2004). Package Insert, Abbott Laboratories, North Chicago, IL, 2 pages.

Isi Web of Science (2005). Tutorial (v6.0), retrieved from the Internet: http://web.archive.org/web/20040228084928/www.isinet.com/tutorials/wos6/wos6tut11.html, last visited Jul. 5, 2024, 1 page.

Jiskoot, W. et al. (2022, e-pub. Nov. 20, 2021). "Ongoing Challenges to Develop High Concentration Monoclonal Antibody-Based Formulation for Subcutaneous Administration: Quo Vadis?" J. of Pharm. Sci. 111:861-867.

Kohn, W.D. et al. (1997). "Salt Effects on Protein Stability: Two-Stranded α-Helical Coiled-Coils Containing Inter- or Intrahelical Ion Pairs," J. Mol. Biol. 267: 1039-1052.

Lanier, B.Q. et al. (2003). "Omalizumab is Effective in the Long-Term Control of Severe Allergic Asthma," Ann. Allergy Asthma Immunol. 91:154-159.

Li, S. et al. (1996). "Effects of Reducing Sugars on the Chemical Stability of Human Relaxin in the Lyophilized State," J. of Pharm. Sci. 85(8):873-877.

Li, S. et al. (996). "Inhibitory Effect of Sugars and Polyols on the Metal-Catalyzed Oxidation of Human Relaxin," J. of Pharm. Sci. 85(8): 868-872.

McLellan, D. et al. (Jan. 1, 2004). "Drug Criteria & Outcomes: Formulary Evaluation of Omalizumab (Xolair)®," Relais Media, 10 pages.

Milgrom, H. et al. (1999). "Treatment of Allergic Asthma with Monoclonal Anti-IgE Antibody," The New England Journal of Medicine 341(26): 1966-1973.

Milgrom, H. et al. (2001). "Treatment of Childhood Asthma with Anti-Immunoglobulin E Antibody (Omalizumab)," Pediatrics 108(2):1-10.

MYLOTARG® [Gemtuxumab Ozogamicon] (undated) Package Insert, Wyeth Laboratories, Philadelphia, PA, 4 pages.

Nelson, D.L. et al. (2000). "Amino Acids, Peptides, and Proteins," in Lehninger Principles of Biochemistry, 3rd Edition, Worth Publishers, New York, NY, Table of Contents and Chapter 5, pp. 115-158, 61 pages.

Nelson, D.L. et al. (2000). "Water," in Lehninger Principles of Biochemistry, 3rd Edition, Worth Publishers, New York, NY, Table of Contents and Chapter 4, pp. 82-114, 47 pages.

OMLYCLO [Omalizumab] (2024). EPAR, Product Information, 87 pages.

Parkins, D.A. et al. (2000). "The Formulation of Biopharmaceutical Products," Pharmaceutical Science & Technology 3(4):129-137.

Randolph, T.W. et al. (2002). "Surfactant-Protein Interactions," in Rational Design of Stable Protein Formations, Carpenter and Manning (eds.), Kluwer Academic/Plenum Publishers, New York, 17 pages.

RAPTIVA® [Efalizumab] (Oct. 2003). Package Insert, Genentech, Inc., South San Francisco, CA, 3 pages.

Reichert, J.M. (2012). "Marketed Therapeutic Antibodies Compendium," mAbs 4(3):413-415.

REMICADE® [Infliximab] (May 2004). Package Insert, Centocor, Inc., Malvern, PA, 3 pages.

REOPRO® [Abciximab] (Nov. 1997). Package Insert, Eli Lilly and Company, Indianapolis, IN, 3 pages.

RITUXAN® [Ritoximab] (Nov. 1997). Package Insert, IDEC Pharmaceuticals Corporation, San Diego, CA and Genentech, Inc., South San Francisco, CA, 2 pages.

Roefs, S.P.F.M. et al. (1994). "A Model for the Denaturation and Aggregation of β-Lactoglobulin," Eur. J. Biochem. 226:883-889.

Roskos, L.K. et al. (2004). "The Clinical Pharmacology of Therapeutic Monoclonal Antibodies," Drug Development Research 61:108-120.

Shire, S.J. et al. (2004). "Challenges in the Development of High Protein Concentration Formulations," J. of Pharm. Sci. 93(6):1390-1402.

SIGMA-ALDRICH (Jun. 28, 2024). Product Specification of L-Histidine Monohydrochloride Monohydrate, H5659, 2 pages.

SIGMA-ALDRICH (Jun. 28, 2024). Product Specification of L-Histidine, H8000, 1 page.

SIMULECT® [Basiliximab] (Nov. 2003). Package Insert, Novartis Pharmaceuticals Corporation, East Hanover, NJ, 5 pages.

Solèr, M. et al. (2001). "The Anti-IgE Antibody Omalizumab Reduces Exacerbations and Steroid Requirement in Allergic Asthmatics," Eur. Respir J. 18:254-261.

Strickley, R.G. et al. (2021, e-pub. Mar. 28, 2021). "A Review of Formulations of Commercially Available Antibodies," J. of Pharm. Sci. 110:2590-2608, 75 pages.

SYNAGIS® [Palivizumab] (Dec. 1999). Package Insert, MedImmune, Inc., Gaithersburg, MD and Ross Products Division of Abbott Laboratories, Inc., Columbus, OH, 3 pages.

U.S. Pharmacopeial Convention (2002). USP NF, United States Pharmacopeia, "1049—Quality of Biotechnological Products: Stability Testing of Biotechnological Biological Products," 7 pages.

U.S. Pharmacopeial Convention (2003) USP Dictionary of USAN and International Drug Names, U.S. Pharmacopeia, Omalizumab, 6 pages.

Voet, D. et al. (1999). "Water," Fundamentals of Biochemistry, 1st Edition, Table of Contents and Chapter 2, pp. 23-38, 30 pages.

XOLAIR® (2023). Excerpt from EPAR Product Information for Omalizumab, 2 pages.

XOLAIR® (2024) Instructions for Use Prefilled Syringe, 39 pages.

XOLAIR® (2024). European Medicines Agency screenshot, retrieved from the Internet, https://www.erna.europa.eu/en/medicines/human/EPAR/xolair, last visited Aug. 12, 2024, 8 pages.

XOLAIR® (2024). Omalizumab: Description and Brand Names, Mayo Clinic screenshot, retrieved from the Internet https://www.mayclinic.org/drugs-supplements/omalizumab-subcutaneous-route/proper-use/drg-20065207?p=1, last visited Aug. 11, 2024, 5 pages.

XOLAIR® [Omalizumab] (2003). Package Insert, Genentech, Inc., South San Francisco, CA and Novartis Pharmaceuticals Corporation, East Hanover, NJ, 2 pages.

ZENAPAX® [Daclizumab] (Jul. 2003). Package Insert, Hoffmann-La Roche Inc., Nutley, NJ, 3 pages.

ZEVALIN® [Ibritumomab Tiuxetan] (Dec. 2001). Package Insert, IDEC Pharmaceuticals Corporation, San Diego, CA, 7 pages.

European Patent No. 3805248 B1 (EP Appln. No. 20200642.5) Letter from Opponent 1 filed by Celltrion, Inc. in Opposition Proceedings on Jul. 3, 2024, 60 pages.

European Patent No. 3805248 B1 (EP Appln. No. 20200642.5) Letter from Patentees filed by Genentech, Inc. & Novartis AG in Opposition Proceedings on Aug. 5, 2024, 10 pages.

European Patent No. 3805248 B1 (EP Appln. No. 20200642.5) Letter from Opponent 1 filed by Celltrion, Inc. in Opposition Proceedings on Aug. 16, 2024, 53 pages.

European Patent No. 3805248 B1 (EP Appln. No. 20200642.5) Summons to Attend Oral Proceedings Pursuant to Rule 115(1) EPC mailed in Opposition Proceedings on Sep. 2, 2024, 33 pages.

AllergyUK (Sep. 2021). "Your Quick Guide To: Peanut Allergy," 4 pages.

(56) References Cited

OTHER PUBLICATIONS

Borchers, A.T. et al. (2004). "The Diagnosis and Management of Anaphylaxis," Comp. Ther. 30(2):111-120.
British National Formulary 47 (Mar. 2004) British Medical Association, Royal Pharmaceuticals of Great Britian, 4 pages.
British National Formulary 48 (Sep. 2004) British Medical Association, Royal Pharmaceuticals of Great Britian, 5 pages.
Buchner, J. et al. (1991). "Renaturation, Purification and Characterization of Recombinant Fab-Fragments Produced in *Escherichia Coli*," Bio/Technology 9:157-162.
Carpenter, J.F. et al. (2002). "Rational Design of Stable Protein Formulations: Theory and Practice," Pharmaceutical Biotechnology, Preface and Table of Contents, 11 pages.
Carpenter, J.F. et al. (2002) "Chapter 5—Rational Design of Stable Protein Formulations: Theory and Practice," In Carpenter & Manning (eds.) Rational Design of Stable Protein Formulations, pp. 109-133.
Dalby, I. (2016) "Enable Rapid Liquid and Freeze-Dried Formulation Design for the Manufacture and Delivery of Novel Biopharmaceuticals," EPSRC Reference: EP/N025105/1, Details of Grant, 2 pages.
Davis, L.A. (2004, e-pub. Jun. 8, 2004). "Omalizumab: A Novel Therapy for Allergic Asthma," Ann. Pharmacother. 38:1236-1242.
European Medicines Agency (2007). European Public Assessment Report (EPAR) Raptiva, 3 pages.
European Medicines Agency (2019). Summary of Opinion on REMSIMA [Infliximab], 1 page.
European Patent No. 3370770 B1 (EP Appln. No. 16862791.7) Expert Declaration of Paul Dalby, dated May 2002, filed by Janssen Biotech, Inc. in Opposition Proceedings on May 12, 2022, 20 pages.
European Patent No. 3805248 B1 (EP Appln. No. 20200642.5) Third Expert Declaration of H.W. Frijlink, dated Sep. 3, 2024, filed in *Celltrion Inc. & Celltrion Healthcare B.V. v. Novartis AG & Genentech, Inc.*, District Court in The Hague, Netherlands, 13 pages.
European Patent No. 3805248 B1 (EP Appln. No. 20200642.5) Declaration of A. Obermeier, dated Sep. 3, 2024, filed in *Celltrion Inc. & Celltrion Healthcare B.V. v. Novartis AG & Genentech, Inc.*, District Court in The Hague, Netherlands, 6 pages.
European Patent No. 3805248 B1 (EP Appln. No. 20200642.5) Declaration of D. Crommelin, dated Sep. 13, 2024, in *Novartis AG & Genentech, Inc. v. Celltrion Inc. & Celltrion Healthcare B.V.*, District Court in The Hague, Netherlands, Original Dutch reference with English translation, 30 pages.
European Patent No. 3805248 B1 (EP Appln. No. 20200642.5) Fourth Expert Declaration of H.W. Frijlink, dated Oct. 22, 2024, filed in *Celltrion Inc. & Celltrion Healthcare B.V. v. Novartis AG & Genentech, Inc.*, Court in The Hague, Netherlands, 16 pages.
European Patent No. 3805248 B1 (EP Appln. No. 20200642.5) Expert Report and CV of Neil Barnes, dated Jul. 4, 2024, filed in *Celltrion Inc. v. Genentech, Inc. & Novartis AG*, in The High Court Of Justice, Business And Property Courts Of England And Wales, 96 pages.
European Patent No. 3805248 B1 (EP Appln. No. 20200642.5) Expert Report and CV of Paul Dalby, dated Jul. 5, 2024, filed in *Celltrion Inc. v. Genentech, Inc. & Novartis AG*, in The High Court Of Justice, Business And Property Courts Of England And Wales, 97 pages.
European Patent No. 3805248 B1 (EP Appln. No. 20200642.5) Expert Report and CV of Ian Pavord, dated Jul. 5, 2024, filed in *Celltrion Inc. v. Genentech, Inc. & Novartis AG*, in The High Court Of Justice, Business And Property Courts Of England And Wales, 78 pages.
European Patent No. 3805248 B1 (EP Appln. No. 20200642.5) Expert Report and CV of Bernhardt Levy Trout, dated Jul. 5, 2024, filed in *Celltrion Inc. v. Genentech, Inc. & Novartis AG*, in The High Court Of Justice, Business And Property Courts Of England And Wales, 92 pages.
European Patent No. 3805248 B1 (EP Appln. No. 20200642.5) Second Expert Report of Neil Barnes, dated Aug. 9, 2024, filed in *Celltrion Inc. v. Genentech, Inc. & Novartis AG*, in The High Court Of Justice, Business And Property Courts Of England And Wales, 8 pages.
European Patent No. 3805248 B1 (EP Appln. No. 20200642.5) Second Expert Report of Paul Dalby, dated Aug. 9, 2024, filed in *Celltrion Inc. v. Genentech, Inc. & Novartis AG*, in The High Court Of Justice, Business And Property Courts Of England And Wales, 12 pages.
European Patent No. 3805248 B1 (Ep Appln. No. 20200642.5) Second Expert Report of Ian Pavord, dated Aug. 9, 2024, filed in *Celltrion Inc. v. Genentech, Inc. & Novartis AG*, in The High Court Of Justice, Business And Property Courts Of England And Wales, 7 pages.
European Patent No. 3805248 B1 (EP Appln. No. 20200642.5) Second Expert Report of Bernhardt Levy Trout dated Aug. 9, 2024 with redactions, filed in *Celltrion Inc. v. Genentech, Inc. & Novartis AG*, in The High Court Of Justice, Business And Property Courts Of England And Wales, 29 pages.
European Patent No. 3805248 B1 (EP Appln. No. 20200642.5) Third Expert Report of Ian Pavord, dated Oct. 21, 2024, filed in *Celltrion Inc. v. Genentech, Inc. & Novartis AG*, in The High Court Of Justice, Business And Property Courts Of England And Wales, 2 pages.
European Patent No. 41082259 B1 (EP Appln. No. 22178117.2) Response to Summons to Attend Oral Proceedings, Sep. 27, 2023, 3 pages.
European Patent No. 41082259 B1 (EP Appln. No. 22178117.2) Communication of a Notice of Opposition pursuant to Rule 79(2) EPC by Celltrion, Inc., Oct. 9, 2024, 27 pages.
European Respiratory Annual Society Congress from Sep. 4-8, 2004, Glasgow, Scotland, Scientific Programme, 16 pages.
Green, R.H. et al. (2003). "Management of Asthma in Adults: Current Therapy and Future Directions," Postgrad Med. J. 79:259-267.
Hermeling, S. et al. (2003). "Micelle-Associated Protein in Epoetin Formulations: A Risk Factor for Immunogenicity?" Pharmaceutical Research 20(12): 1903-1907.
Jang, J. (Jan. 14, 2019). "Celltrion Applies for 'Remsima SC' Patents in 90 Countries," Press@Bios.co.kr, 3 pages.
Maurer, M. et al. (2022). "Pharmacokinetic Equivalence of CT-P39 and Reference Omalizumab in Healthy Individuals: A Randomised, Double-Blind, Parallel-Group, Phase 1 Trial," Clin. Transl. Allergy e12204, 9 pages.
MERCK Safety Data Sheet for Polysorbate 20 (2022), 10 pages.
Mieczkowski, C.A. et al. (2023, e-pub. Apr. 8, 2023). "The Evolution of Commercial Antibody Formulations," Journal of Pharmaceutical Sciences 112:1801-1810.
Mittal, K.L. (1970). "Determination of CMC of Polysorbate 20 in Aqueous Solution by Surface Tension Method," Journal of Pharmaceutical Sciences, 61(8): 1334-1335.
Oxford BRC Screenshot of "Breakthroughs in Asthma Treatment" YouTube video of I. Pavord, dated May 30, 2019, 1 page.
Pandya, A. et al. (2018). "An Evaluation of the Potential of NMR Spectroscopy and Computational Modelling Methods to Inform Biopharmaceutical Formulations," Pharmaceutics 10:165, 24 pages.
Ruffin, C.G. et al. (Jul. 15, 2004). "Omalizumab: A Recombinant Humanized Anti-IgE Antibody for Allergic Asthma," Am. J. Health-Syst. Pharm. 61:1449-1459.
U.S. Appl. No. 10/813,483, Declaration and CV of Jun Liu, dated Sep. 4, 2008, 11 pages.
U.S. Pat. No. 8,562,999 Declaration, CV and List of Materials Considered of Paul Dalby, dated Sep. 13, 2017, filed by Wyeth LLC in Inter Partes Review Case No. IPR No. 2017-00378, 87 pages.
U.S. Pat. No. 8,580,264 Transcript of Deposition of Paul Dalby, dated Dec. 2, 2022, filed by Celltrion, Inc. in Inter Partes Review Case No. IPR No. 2022-00578, 23 pages.
Zarbin, M. (2020). "The Development Pathway for Biosimilar Biotherapeutics," J. Ophthalmic Vis. Res. 15 (3):273-274.

PROCESS FOR CONCENTRATION OF ANTIBODIES AND THERAPEUTIC PRODUCTS THEREOF

RELATED APPLICATIONS

This application is a continuation of U.S. patent application Ser. No. 16/752,366, filed on Jan. 24, 2020, which is a continuation of U.S. patent application Ser. No. 16/447,800, filed Jun. 20, 2019, now abandoned, which is a continuation of U.S. patent application Ser. No. 14/257,907, filed Apr. 21, 2014, now U.S. Pat. No. 10,370,456, which is a continuation application of U.S. patent application Ser. No. 11/220,362, filed Sep. 6, 2005, now abandoned, which claims the priority benefit of U.S. Provisional Application No. 60/609,092 filed Sep. 9, 2004, all of which are incorporated herein by reference in their entirety.

BACKGROUND

Methods for isolating, purifying, and concentrating biological materials are known and include, for example, chromatography, ultrafiltration, and lyophilization, see generally, R. Hatti-Kaul et al., "Downstream Processing in Biotechnology," in *Basic Biotechnology*, Chap. 9, pages 187-211, 2nd ed., Cambridge University Press (2001). Processes for making concentrated monoclonal antibody preparations for administration to humans are known, see for example, U.S. Pat. No. 6,252,055, which uses ultrafiltration and which re-circulates the resulting filtrate.

Some challenges associated with available antibody concentration methods include, for example, low fluxes, long process times, large membrane areas, mechanical recovery yield and losses, operator-intensive intervention or handling, low mass transfer rates, energy inefficiencies, and hydraulic pressure limits on concentration equipment. These and other challenges can contribute to a high total cost of manufacture and ultimately higher costs to therapeutic drug consumers.

There is a need for improved processes for preparing highly concentrated protein formulations, such as liquid antibody preparations and therapeutic products thereof.

SUMMARY

In general terms, the present disclosure generally relates to processes for concentrating proteins, such as processes for concentrating an antibody preparation, pharmaceutical formulations containing such a preparation, and there use in human therapy or animal therapy.

In embodiments the present disclosure provides processes for preparing highly concentrated proteins, such as antibody preparations; and therapeutic products prepared by the process, such as therapeutic antibody products. Accordingly, the present disclosure provides, a process for concentrating proteins comprising: a first ultrafiltering of a first antibody preparation to provide a second antibody preparation; a diafiltering the second antibody preparation to provide a diafiltered intermediate antibody preparation; and a second ultrafiltering of the diafiltered intermediate antibody preparation to provide a third antibody preparation, wherein one or more of the first ultrafiltering, the second ultrafiltering, and the diafiltering are accomplished at elevated temperatures, for example, from about 30° C. to about 50° C.

The present disclosure also provides, in embodiments, a process for concentrating proteins comprising: a first ultrafiltering of a first protein mixture to provide a second protein mixture; a diafiltering the second protein mixture to provide a diafiltered protein mixture; and a second ultrafiltering of the diafiltered protein mixture to provide a third protein mixture, wherein one or more of the first ultrafiltering, the diafiltering, and the second ultrafiltering are accomplished at, for example, about 45° C.

The present disclosure also provides, in embodiments, a highly concentrated antibody composition prepared by the above processes.

DETAILED DESCRIPTION

Figure 1:
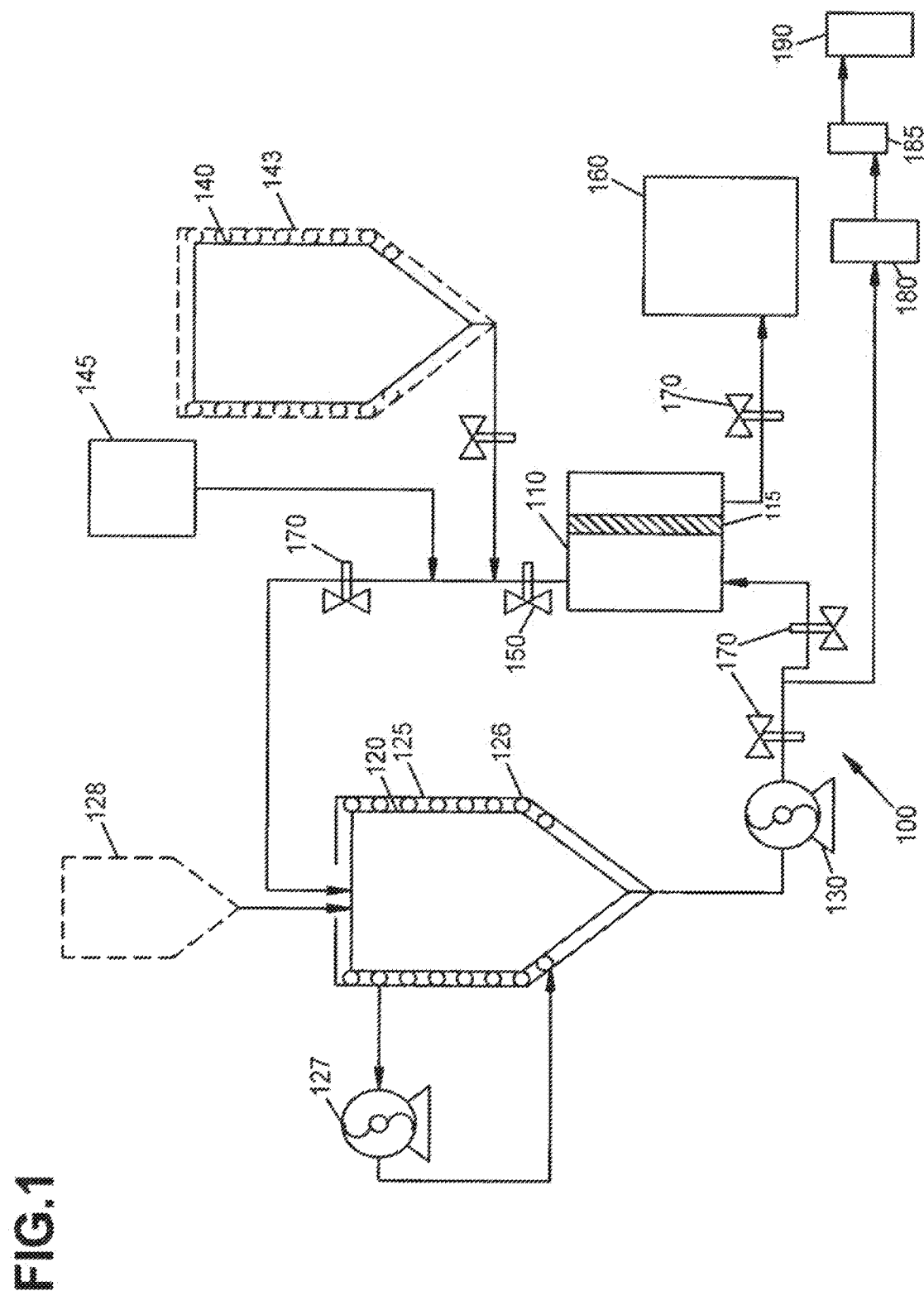
FIG. 1 illustrates an apparatus for accomplishing the preparative process, in embodiments of the present disclosure.

Various embodiments of the present disclosure will be described in detail with reference to drawings, if any. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

The following are used, unless otherwise described:

"Ultrafiltering," "ultrafiltration," "ultrafiltered," "UF," and like terms refer to, for example, using synthetic semipermeable membranes, with appropriate physical and chemical properties, to discriminate between molecules in the mixture, primarily on the basis of molecular size and shape, and accomplish separation of different molecules or accomplish concentration of like molecules.

"Diafiltering," "diafiltration," "diafiltered," "diafiltrating," "DF," and like terms refer to, for example, using an ultrafiltration membrane to remove, replace, or lower the concentration of salts or solvents from solutions or mixtures containing proteins, peptides, nucleic acids, or other biomolecules.

"Transmembrane pressure" or "TMP" refers to the average applied pressure from the feed to the filtrate side of the membrane calculated as TMP $[bar]=[(P_F+P_R)/2]-P_f$, where $P_F$ is the feed pressure, $P_R$ is the retentate pressure, and $P_f$ is the filtrate pressure.

"Tangential flow filtration," "cross flow filtration," "TFF," and like terms refer to a mode of filtration in which the solute-containing solution passes tangentially across the UF membrane and lower molecular weigh salts or solutes are passed through by applying pressure.

"Antibody" is used in the broadest sense and specifically covers intact monoclonal antibodies, polyclonal antibodies, multispecific antibodies (e.g., bispecific antibodies) formed from at least two intact antibodies, and antibody fragments, so long as they exhibit the desired biological activity. An antibody is a protein generated by the immune system that is capable of recognizing and binding to a specific antigen. Described in terms of its structure, an antibody is a Y-shaped protein consisting of four amino acid chains, two heavy and two light. In a simplified model sufficient for this appeal, each antibody has primarily two regions: a variable region and a constant region. The variable region, located on the ends of the arms of the Y, binds to and interacts with the target antigen. This variable region includes a complementary determining region (CDR) that recognizes and binds to a specific binding site on a particular antigen. The constant region, located on the tail of the Y, is recognized by and interacts with the immune system (Janeway, C., Travers, P., Walport, M., Shlomchik (2001) *Immuno Biology, 5th Ed.*, Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th edition, D. Stites, A. Terr and T. Parslow (eds.), Appleton & Lange, Norwalk, CT, 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the approximately 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., in *Sequences of Proteins of Immunological Interest*, 5th Ed. Public Health Service, National Institutes of Health, Bethesda, MD (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g., around about Kabat residues 24-34 (L1), 50-56 (L2) and 89-97 (L3) in the $V_L$, and around about Kabat residues 31-35B (H1), 50-65 (H2) and 95-102 (H3) in the $V_H$ (see Kabat et al., supra) and/or those residues from a "hypervariable loop" (e.g., around about Chothia residues 26-32 (L1), 50-52 (L2) and 91-96 (L3) in the $V_L$, and 26-32 (H1), 52A-55 (H2) and 96-101 (H3) in the $V_H$ (Chothia and Lesk, *J. Mol. Biol.*, 196:901-917 (1987)).

The term "monoclonal antibody" as used herein refers to an antibody from a population of substantially homogeneous antibodies, i.e., the individual antibodies comprising the population are identical and/or bind the same epitope(s), except for possible variants that may arise during production of the monoclonal antibody, such variants generally being present in minor amounts. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., *Nature,* 256:495 (1975); Harlow et al., *Antibodies: A Laboratory Manual,* (Cold Spring Harbor Laboratory Press, 2nd ed. 1988); Hammerling et al., in: *Monoclonal Antibodies and T-Cell Hybridomas,* 563-681, (Elsevier, N.Y., 1981)), recombinant DNA methods (see, e.g., U.S. Pat. No. 4,816,567), phage display technologies (see, e.g., Clackson et al., *Nature,* 352:624-628 (1991); Marks et al., *J. Mol. Biol.,* 222:581-597 (1991); Sidhu et al., *J. Mol. Biol.* 338(2):299-310 (2004); Lee et al., *J. Mol. Biol.* 340(5):1073-1093 (2004); Fellouse, *Proc. Nat. Acad. Sci. USA* 101(34):12467-12472 (2004); and Lee et al., *J. Immunol. Methods* 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits, et al., *Proc. Natl. Acad. Sci. USA,* 90:2551 (1993); Jakobovits, et al., *Nature,* 362:255-258 (1993); Bruggemann, et al., *Year in Immuno.,* 7:33 (1993); U.S. Pat. Nos. 5,545,806; 5,569,825; 5,591,669 (all to GenPharm); U.S. Pat. No. 5,545,807; WO 1997/17852; U.S. Pat. Nos. 5,545,807; 5,545,806; 5,569,825; 5,625,126; 5,633,425; and 5,661,016; Marks, et al., *Bio/Technology,* 10: 779-783 (1992); Lonberg, et al., *Nature,* 368: 856-859 (1994); Morrison, *Nature,* 368: 812-813 (1994); Fishwild, et al., *Nature Biotechnology,* 14: 845-851 (1996); Neuberger, *Nature Biotechnology,* 14: 826 (1996); and Lonberg and Huszar, *Intern. Rev. Immunol.,* 13: 65-93 (1995).

"Chimeric" antibodies (immunoglobulins) have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison, et al., *Proc. Natl. Acad. Sci. USA* 81:6851-6855 (1984)). Humanized antibody as used herein is a subset of chimeric antibodies.

"Humanized" forms of non-human (e.g., murine) antibodies are chimeric antibodies which contain minimal sequence derived from non-human immunoglobulin. For the most part, humanized antibodies are human immunoglobulins (recipient or acceptor antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence although the FR regions may include one or more amino acid substitutions that improve binding affinity. The number of these amino acid substitutions in the FR are typically no more than 6 in the H chain, and in the L chain, no more than 3. The humanized antibody optionally also will comprise at least a portion of an immunoglobulin constant region (Fc), typically that of a human immunoglobulin. For further details, see Jones, et al., *Nature* 321:522-525 (1986); Reichmann, et al., *Nature* 332:323-329 (1988); and Presta, *Curr. Op. Struct. Biol.* 2:593-596 (1992).

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata, et al., *Protein Eng.,* 8(10): 1057-1062 (1995)); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies,* vol. 113, Rosenburg and Moore eds., Springer-Verlag, New York, pp. 269-315 (1994).

"About" modifying, for example, the quantity of an ingredient in the compositions, concentration of an active, buffer volumes, diavolumes, pore size, apparent molecular, molecular weight cut-off, process temperature, process time, yields, flow rates, pressures, bio-burdens, and like values, and ranges thereof, employed in the methods of the invention, refers to variation in the numerical quantity that can occur, for example, through typical measuring and handling procedures used for making concentrates or use solutions; through inadvertent error in these procedures; through differences in the manufacture, source, or purity of the ingredients employed to make the compositions or carry out the methods; and like considerations. The term "about" also encompasses amounts that differ due to aging of a composition with a particular initial concentration or mixture. The term "about" also encompasses amounts that differ due to mixing or processing a composition with a particular initial concentration or mixture. Whether or not modified by the term "about" the claims include equivalents to the quantities.

"Consisting essentially of" refers to a process of obtaining a concentrated protein composition or antibody composition that includes the steps and ingredients listed in the claim, plus other steps and ingredients that do not materially affect the basic and novel properties of the composition, such as a multiplicity of steps or buffer media. Ingredients that materially affect the basic properties of the composition and method of the present disclosure impart undesirable characteristics including, for example, bio-burden, such as the undesirable toxicity or irritability associated with contaminants.

The indefinite article "a" or "an" and its corresponding definite article "the" as used herein is understood to mean at least one, or one or more, unless specified otherwise.

The present disclosure provides, in embodiments, the abovementioned processes and the concentrated antibody products thereof.

In embodiments of the present disclosure, the preparative processes and products thereof can be used in preparing highly concentrated antibody preparations and similar preparations, such as purifying and concentrating proteins or like substances from natural or synthetic sources, and which products can be useful for treating pathological conditions, such as asthma, cancer, psoriasis, inhibiting angiogenesis, and like pathological conditions.

In embodiments of the above-mentioned process for preparing highly concentrated antibody compositions of the disclosure, the following further exemplifies how to make and use the preparative processes and products of the disclosure.

In embodiments of the present disclosure, there is provided a process for preparing highly concentrated antibody compositions, for example, according to accomplishing the following steps in the order recited, comprising:
  a first ultrafiltering of a first antibody preparation, having a concentration of, for example, about 0.1 to about 10 grams per liter (g/L), to provide an second antibody preparation as the retentate, having a greater antibody concentration of, for example, about 10 to about 50 grams per liter;
  a diafiltering of the resulting second antibody preparation to provide a diafiltered intermediate antibody preparation as the retentate, having about the same concentration as the resulting second antibody preparation retentate, that is, diafiltering to accomplish a buffer exchange at constant volume; and
  a second ultrafiltering of the diafiltered intermediate antibody preparation to provide a third antibody preparation as the retentate, having a greater antibody concentration of, for example, about 150 to about 200 grams per liter.

The preparative processes of the disclosure can further comprise an optional product recovery step or steps, for example, and as disclosed and illustrated herein.

In embodiments of the above-mentioned process of the disclosure, one or more of the first ultrafiltering, the diafiltering, and the second ultrafiltering, can be accomplished at, for example, from about 30° C. to about 70° C. In embodiments, these steps can also be accomplished at, for example, from about 30° C. to about 50° C. In embodiments, these steps can also be accomplished at, for example, from about 35° C. to about 50° C. In embodiments, these steps can also be accomplished at, for example, about 45° C., such as from about 45° C. plus or minus 5° C. Depending upon the type of antibody preparation, for processes accomplished at temperatures above about 70° C., the preparation may show signs of deterioration, such as denaturation, agglomeration, and like phenomena. For processes accomplished at temperatures below from about 30 to about 35° C., the flow rates are typically undesirably low and process times are undesirably long, making the process at lower temperatures less attractive for efficient commercial production.

In embodiments, the first antibody preparation can have an antibody concentration of, for example, from about 0.1 to about 100 grams per liter (g/L). The antibody concentration is, for example, a common concentration typically available from other preliminary protein or antibody purification steps or methods, such as, centrifugation, filtration, chromatography, and like procedures. The resulting second antibody preparation obtainable from the first ultrafiltering can have an antibody concentration of, for example, from about 10 to about 50 grams per liter, and for example, about 20 to about 40 grams per liter, such as 30 grams per liter. A range for the antibody concentration of the intermediate antibody preparation can depend upon, for example, a balance of factors, such as sample volume and sample flux achievable with a particular buffer containing the second antibody preparation. The intermediate antibody preparation can have an antibody concentration of, for example, about 25 to about 35 grams per liter and the third antibody preparation can have an antibody concentration of, for example, from about 170 to about 200 grams per liter. The third antibody preparation, in embodiments, can have an antibody concentration of, for example, from about 50 to about 250 grams per liter, such as from of about 100 to about 230 grams per liter, and from about 170 to about 200 grams per liter, such as 185 grams per liter.

It will be apparent to one skilled in the art, upon comprehending the present disclosure, that the intermediate antibody preparation and third antibody preparation comprise the same ultra-filtered retentate except for, for example, differences in the antibody concentration resulting from the first and second ultrafiltering concentration, and differences in the suspending buffer media resulting from the diafiltration buffer exchange. Thus, there is little, if any, compositional change, such as degradation, of the target protein or antibody product, in embodiments of the present disclosure.

Conventional ultrafiltration concentration methods can have generally greater time and lesser through-put inefficiencies having considerably longer process times such as several days to several weeks, process considerably smaller volumes, or both.

In embodiments, the protein concentration process of the disclosure can be accomplished in, for example, from about 1 to 10 hours, preferably in from about 2 to 5 hours, and more preferably in about 3 hours. The preferences favor higher flux through-put and smaller membrane areas.

In embodiments, the first ultrafiltering can be accomplished, for example, in about 35 percent of the total process time. Thus, for example, in a concentration and purification process of the disclosure with about 3 hours total process time, the first ultrafiltering can be accomplished in about 45 minutes. In embodiments, the second ultrafiltering can be accomplished, for example, in about 15 percent of the total process time. Thus, for example, in a process of the disclosure with about 3 hours total process time, the second ultrafiltering can be accomplished in about 15 minutes. The diafiltering can be accomplished, for example, in about 50 percent of the total process time. Thus, for example, in a process of the disclosure with about 3 hours total process time, the diafiltering can be accomplished in from about 90 to about 120 minutes.

In embodiments, the first ultrafiltering and the second ultrafiltering can be accomplished, for example, with an ultra-filter membrane having a nominal pore size, or molecular weight cut-off, of about 5 to about 50 kiloDaltons. Another suitable nominal pore size is, for example, from about 10 to about 40 kiloDaltons. Yet another suitable nominal pore size, or molecular weight cut-off, is about 30 kiloDaltons.

In embodiments, the first antibody preparation can contain, for example, an antibody having an apparent molecular weight of, for example, about 100 to about 200 kiloDaltons. In other embodiments, the first antibody preparation can contain an antibody having an apparent molecular weight of, for example, about 150 kiloDaltons, such as when the antibody preparation comprises anti-IgE antibodies or IgE, see for example, U.S. Pat. No. 6,172,213 assigned to Genentech, Inc.

Other antibodies suitable for use in the present disclosure include cancer eating antibodies, see generally, for example: PCT/US02/19592; PCT/US01/20118; PCT/US01/25464; PCT/US01/26626; PCT/US02/28859; PCT/US02/41798; PCT/US02/12206; PCT/US03/11148; PCT/US02/12619; and PCT/US02/33050. Still other antibodies suitable for use in the present disclosure include an anti-CD20 antibody and like antibodies including human, non-human, murine, hybrid, and chimeric forms. See for example U.S. Pat. No. 6,582,959 (VEGF) and U.S. Patent Application No. 2002/0122797 A1 (human VEGF).

In embodiments, antibodies included within the scope of the disclosure include hybrid and recombinant antibodies (e.g., "humanized" and "human" antibodies) regardless of species of origin or immunoglobulin class or subclass designation, as well as antibody fragments (for example, Fab, F(ab')$_2$, and F$_v$). See U.S. Pat. No. 4,816,567; Mage and Lamoyi, in *Monoclonal Antibody Production Techniques and Applications*, 79-97, Marcel Dekker, Inc., New York, (1987).

Monoclonal antibodies may also be used and can be isolated from phage antibody libraries using the techniques described in Clackson et al (1991) *Nature*, 352:624-628 and Marks, et al. (1991) *J. Mol. Biol.*, 222:581-597, for example. Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison, et al. (1984) *Proc. Natl. Acad. Sci. USA*, 81:6851-6855). Chimeric antibodies can include "primatized" antibodies comprising variable domain antigen-binding sequences derived from a non-human primate (e.g., Old World Monkey, Ape etc) and human constant region sequences.

Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. Thus, the modifier "monoclonal" indicates the character of the antibody as being obtained from such a substantially homogeneous population of antibodies, i.e., the individual antibodies comprising the population are identical except for possible naturally occurring mutations that may be present in minor amounts, and is not to be construed as requiring production of the antibody by any particular method. For example, the monoclonal antibodies for use in the disclosure may be made using the hybridoma method first described by Kohler & Milstein, *Nature*, 256:495 (1975), or may be made by recombinant DNA methods. Other known methods of antibody production are described, for example, in Goding, *Monoclonal Antibodies: Principles and Practice*, 59-103, Academic Press (1986); Kozbor, *J. Immunol.*, 133:3001 (1984), Brodeur, et al., *Monoclonal Antibody Production Techniques and Applications*, 51-63, Marcel Dekker, Inc., New York (1987).

Various methods have been employed to produce monoclonal antibodies (MAbs). Hybridoma technology, which refers to a cloned cell line that produces a single type of antibody, uses the cells of various species, including mice (murine), hamsters, rats, and humans. Another method to prepare MAbs uses genetic engineering including recombinant DNA techniques. Monoclonal antibodies made from these techniques include, among others, chimeric antibodies and humanized antibodies. A chimeric antibody combines DNA encoding regions from more than one type of species. For example, a chimeric antibody may derive the variable region from a mouse and the constant region from a human. A humanized antibody comes predominantly from a human, even though it contains nonhuman portions. Like a chimeric antibody, a humanized antibody may contain a completely human constant region. But unlike a chimeric antibody, the variable region may be partially derived from a human. The nonhuman, synthetic portions of a humanized antibody often come from CDRs in murine antibodies. In any event, these regions are crucial to allow the antibody to recognize and bind to a specific antigen.

As noted, murine antibodies play an important role in antibody technology. While useful for diagnostics and short-term therapies, murine antibodies cannot be administered to people long-term without increasing the risk of a deleterious immunogenic response. This response, called Human Anti-Mouse Antibody (HAMA), occurs when a human immune system recognizes the murine antibody as foreign and attacks it. A HAMA response can cause toxic shock or even death. Chimeric and humanized antibodies reduce the likelihood of a HAMA response by minimizing the nonhuman portions of administered antibodies. Furthermore, chimeric and humanized antibodies have the additional benefit of activating secondary human immune responses, such as antibody dependent cellular cytotoxicity.

An "intact" antibody is one that comprises an antigen-binding variable region as well as a light chain constant domain (CL) and heavy chain constant domains, CH1, CH2 and CH3. The constant domains may be native sequence constant domains (e.g., human native sequence constant domains) or amino acid sequence variant thereof. The intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g., B cell receptor; BCR), etc.

Depending on the amino acid sequence of the constant domain of their heavy chains, intact antibodies can be assigned to different "classes." There are five major classes of intact antibodies: IgA, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called $\alpha$, $\delta$, $\epsilon$, $\gamma$, and $\mu$, respectively. The subunit structures and three-dimensional configurations of different classes of immunoglobulins are well known.

In embodiments, the first ultrafiltering concentrates the first antibody preparation to provide the second antibody preparation having an antibody concentration of about 30 grams per liter, and the second ultrafiltering concentrates the intermediate antibody preparation (obtained from diafiltering) to provide the third antibody preparation having an antibody concentration of, for example, about 170 to about 200 grams per liter. The first ultrafiltering and the second ultrafiltering can be accomplished with the same ultra-filter membrane, and if desired, within the same vessel or process circuit, for example, to minimize handling, losses, leakage, and like impacts on yield, efficiency, and economy. The first ultrafiltering and the second ultrafiltering can be accomplished with any suitable ultrafilter apparatus or ultrafilter membrane. Many suitable ultrafilter apparatus and ultrafilter membranes, which are capable of tangential flow filtration (TFF) operation to accomplish the ultrafiltrations and diafiltration, are commercially available, such as from Millipore, Pall Corp., Sartorius, and like vendors. In embodiments, a suitable ultra-filter membrane can be, for example, any regenerated cellulose composite, which composite has a relatively low protein adsorption profile compared to other available ultra-filter membranes, such as, polyethersulfone.

The diafiltering operation exchanges a first buffer composition present in the first and second antibody preparations for a second buffer desired in the third antibody preparation. In embodiments, the first buffer can comprise, for example, a mixture of aqueous sodium chloride and a TRIS buffer, and the second buffer can comprise, for example, a mixture of aqueous histidine chloride and arginine chloride. The diafiltering can accomplish a buffer exchange at constant volume, constant concentration, or both. In embodiments, the diafiltering accomplishes a buffer exchange at constant volume and constant concentration. The diafiltering can accomplish a buffer exchange, for example, of from about 5 to about 15 fold volumes (i.e. diavolumes). The diafiltering can also accomplish a buffer exchange, for example, of about 8-fold volumes (8 diavolumes), that is, 8 times the volume of the sample containing the antibody preparation to be exchanged. For example, a 10 liter antibody preparation can be diafiltered with a 5 fold (diavolumes) or 50 liter volume of exchange buffer. The exchange volume and preferences for exchange volumes considers a balance of factors, for example, process through-put efficiencies, product purity, governmental and customer-patient acceptability standards, and like standards, and can depend on, for example, the concentration and type of buffer (e.g., the first buffer) in the first antibody preparation, and like considerations.

The first ultrafiltering, the second ultrafiltering, and the diafiltering are preferably accomplished with tangential flow filtration (TFF mode) across an ultra-filter membrane, and the ultra-filter membrane is preferably the same membrane for each step. The yield of product in the final pool (i.e., the third antibody preparation) can be, for example, greater than about 70 weight percent, such as from about 80 to about 100 weight percent based on the weight of antibodies in the first antibody preparation. The yield of the third antibody preparation can be, in embodiments, greater than about 90 weight %, in embodiments, greater than about 95 weight percent, and in embodiments, even greater than about 98 weight %, based on the weight of antibodies in the first antibody preparation.

The first ultrafiltering can have a recirculation rate of, for example, from about 50 to 1,000 mL/min, and preferably from about 100 to 1,000 mL/min. The recirculation rate can be scaled in accordance with the available membrane area, for example, membrane areas of 5, 20, 200, 1,000 square feet, and like areas permit increasingly higher recirculation rates. Thus, a suitable scaled recirculation rate, in embodiments, can be, for example, from about 0.5 L/min/ft$^2$ to about 5 L/min/ft$^2$. The ultrafiltering and diafiltrating can be accomplished, for example, at transmembrane pressures of from about 5 to about 50 p.s.i. The ultrafiltering and diafiltrating can be accomplished, for example, at transmembrane pressures of from about 10 to about 50 p.s.i. In embodiments of the present disclosure there is provided a process for preparing an antibody concentrate for a more dilute antibody formulation, the antibody concentrate having a minimum bio-burden, for example, of less than or under a detectable limit, such as, less than about 100 CFU/mL.

Antibody compositions of the disclosure can be, for example, concentrated monoclonal antibody preparation for administration to humans, such as at a concentration of greater than or equal to about 100 g/L (mg/mL), such as about 120 to about 170 g/L.

The antibody compositions of the disclosure can be, for example, immunoglobulins, such as from the group IgA, IgD, IgE, IgG, and IgM; sub-classes thereof; recombinants thereof; fragments thereof; and mixtures thereof of any of the foregoing. A preferred antibody composition of the disclosure includes recombinant humanized anti-IgE antibodies. The antibody compositions of the disclosure can include a buffer. A preferred buffer can be, for example, a mixture of aqueous histidine chloride and arginine chloride.

The preparative processes of the disclosure are preferably accomplished in the same apparatus and without operator intervention or with minimal operator intervention, for example, as illustrated in FIG. 1.

The first antibody preparation can be provided or prepared using a variety of chemical, physical, mechanical or non-mechanical, or biochemical methods, such as, grinding, ultrasonication, homogenization, enzymatic digestion, solvent extraction, centrifugation, chromatography, and like methods, and combinations thereof, see for example, the above mentioned R. Hatti-Kaul et al., "Downstream Processing in Biotechnology," in *Basic Biotechnology*, Chap. 9. The third antibody preparation can be further processes, if desired, using for example, nanofiltration (to remove, e.g., divalent ions), reverse osmosis (to remove, e.g., monovalent ions), and like liquid purification methods. The third antibody preparation of the present disclosure can be packaged, stored, or directly used. The third antibody preparation can be further processed, if desired, using for example, additional concentration steps, such as drying, lyophilization, lyophilization-reconstitution, and like methods. The resulting concentrated third antibody product can be reconstituted at a later time, if desired, with a suitable liquid.

Referring to the figures, FIG. 1 illustrates an apparatus, in embodiments of the present disclosure, for accomplishing the preparative process including an ultrafiltration-diafiltration system (100) having an TFF ultra-filtration-diafiltration (UF-DF) unit (110), having a UF-DF membrane (115), which is in communication with recirculation tank (120) which tank serves as a main feed and retentate reservoir. In embodiments, tank (120) can have a temperature control system comprising, for example, an insulating jacket (125), a thermostatic or temperature controlled heating element (126), such as a rheostat resistive heater element or a circulating heated liquid system which includes a heater (not shown), a flow regulator (127), such as a recirculating pump, and a suitable heat transfer fluid, such as either water, glycols, or mixtures thereof. All in-circuit components or component contributing to in-circuit flow or processing, such as pipes, valves, pumps, tanks, and like components, can be optionally insulated or optionally adapted for external heating to maintain close control over temperature specifications and to avoid temperature excursions in the recirculating fluid loop within and between filter chamber (110) and recirculation tank (120). In embodiments, for example, when the system (100) is accomplishing the first ultrafiltration or first ultrafiltering, such as in a fed-batch mode, the system can include an optional feed tank (128) which is in fluid communication with recirculation feed tank (120) and can be used to, for example, make-up, replenish, or supplement the depleted liquid phase from recirculation tank (120).

A pump (130) pumps feed liquid from tank (120) through the UF/DF unit (110) and thereafter recirculates the resulting retentate (the non-filtered or membrane excluded portion of the feed liquid) to recirculating tank (120). A second tank (140) holds and optionally pumps (not shown) a buffer into the main circuit (110-120 loop) during, the constant volume diafiltration. For example, the addition rate and volume of the buffer introduced into the main circuit is preferably at the same rate and volume at which filtrate leaves the main circuit through membrane (115). Buffer tank (140) can be optionally insulated with jacket (143) and can include the equivalent of the abovementioned heating element and a recirculating pump (not shown). An optional inert gas source (145), such as nitrogen, or other compressed gas sources can be used, for example, for product recovery, to pressurize the retentate return, exclude oxygen, for flushing, for cleaning, for membrane integrity testing, and like operations. A third tank (160) is used to collect and recover the filtrate exiting the unit (110). Valves (150, 170) can be used as appropriate to regulate the direction and optionally the liquid flow rate in the system. All values and pumps can be actuated manually, by coordinated computer control, or both. An optional forth tank (190) and exit stream can provide an ancillary waste-flush, product recovery, or monitoring system, for example, when equipped with an optional monitoring device (180), such as an optical density meter, optional filter(s) (185) such as a guard filter, product filter, and like optional subsystems. In embodiments, the main fluid circuit (110-120 loop) can optionally be equipped with an in-line monitoring system.

The concentrated antibody preparations prepared by processes of the present disclosure can be used for human therapeutic administration, including immunoglobulin products, for either intramuscular (IMIG) or intravenous (IVIG) administration. The concentrated antibody preparations of the disclosure can include a stabilizer, for example, a buffered amino acid salt solution, simple sugars, or like stabilizers, suitable ions chelators, such as EDTA or citrate ion, and combinations thereof, see for example, Wang, Y.-C. J. et al, "Parenteral formulations of proteins and peptides: stability and stabilizers," *J Parenteral Sci. Technol.*, 42, Suppl. S3-S26 (1988). Derwent Abstract of JP01268646A (AN89-359879) reports that the application describes an injection preparation of an $IgG_3$ monoclonal antibody having a concentration of 0.1 micrograms/mL to 100 mg/mL. Subject matter disclosed in these publications is believed to be outside the scope of the present disclosure.

Preparations according to the disclosure can be substantially free from aggregates. Acceptable levels of aggregated contaminants would be less than, for example, about 5 weight %, and ideally less than 2 weight %. Levels as low as 0.2 weight % can be achieved, although aggregated contaminants of about 1 weight % is more typical. The preparation in embodiments, can also preferably be free from excipients traditionally used to stabilize polyclonal formulations, for example glycine and/or maltose.

The present disclosure can provide a monoclonal antibody preparation for administration to a human characterized in that the antibody in the preparation is a recombinant antibody and can be at a concentration of 100 mg/mL or greater, preferably greater than 150 mg/mL. The preparation is preferably substantially free from of any protein aggregation.

The pH of pharmaceutical formulations of the disclosure will depend upon the particular route of administration. However, in order to maximize the solubility of the antibody in the concentrated solution, the pH of the solution should be different from the pH of the isoelectric point (pI) of the antibody.

In embodiments of the disclosure, the monoclonal preparation can be envisaged for use in human therapy. Various human disorders can be treated such as cancer or infectious diseases, for example, those mentioned above, and immune dysfunction such as T-cell-mediated disorders including severe vasculitis, rheumatoid arthritis, systemic lupus, also autoimmune disorders such as multiple sclerosis, graft versus host disease, psoriasis, juvenile onset diabetes, Sjogrens' disease, thyroid disease, myasthenia gravis, transplant rejection, inflammatory bowel disease, asthma, IgE mediated disorders, and like disorders or conditions, or combinations thereof.

The disclosure therefore provides in embodiments the use of a concentrated monoclonal antibody preparation as described herein in the manufacture of medicament for the treatment of any of the aforementioned disorders, and like disorders. Also provided is a method of treating a human being, having any such disorder, comprising administering to the individual a therapeutically effective amount of a preparation according to the disclosure. The dosages of such antibody preparations will vary with the conditions being treated and the recipient of the treatment, but can be, for example, in the range of about 50 to about 2,000 mg for an adult patient preferably about 100 to about 1,000 mg administered daily or weekly for a period between 1 and 30 days, and repeated as necessary. The doses may be administered as single or multiple doses.

Process Description. The formulation step typically exchanges the purified bulk drug substance, for example, resulting from ion-exchange chromatography, into the final excipient composition and concentration. There was typically no purification achieved at this step except for small molecule removal. The emphasis was on high yield, buffer exchange, and formulation step robustness. During formulation via TFF (tangential flow filtration), the protein-containing feed solution was pumped through the membrane system and back to the recycle (recirculation) vessel. The TFF membrane retained the protein (as part of the retentate) while the filtrate (or permeate) was driven through the membrane by pressure. The pressure is called the transmembrane pressure (TMP) and is typically controlled using a retentate pressure control valve. The process was usually achieved by a sequence of a first ultrafiltering (concentration), diafiltering (constant volume buffer exchange), and a second ultrafiltering (further concentration). The number of diavolumes (volumetric equivalents) necessary to remove process buffer components can be readily calculated or determined experimentally.

UF/DF Process Generally for anti-IgE. The pH of an anion-exchange pool from chromatography was adjusted to a pH of about 6 using 0.5 M aqueous phosphoric acid. The pH adjusted anion-exchange pool was formulated by ultrafiltration/diafiltration (UF/DF) process of the present disclosure using a membrane having a nominal molecular cut off of 10,000-30,000 Daltons. Prior to processing, the UF membrane was equilibrated with diafiltration buffer (0.02 M histidine, 0.2 M arginine-HCl, pH 6).

The product from an anionic exchange (anion-exchange pool) was then loaded on the system and was concentrated to an intermediate concentration by the first ultrafiltering. The pool was then diafiltered (8× or diavolumes) into its formulation (0.02 M histidine, 0.2 M arginine-HCl, pH 6). The pool was then concentrated by a second ultrafiltering to a final bulk concentration of >170 g/L and recovered through a 0.22 micrometer sterile filter. The entire UF/DF process was performed at a temperature set point of about 45 degrees C. This temperature control was achieved using temperature control of the incoming anion-exchange pool, the diafiltration buffer, and the use of a jacketed recirculation vessel for the UF/DF process as illustrated herein.

After UF/DF, the recovered pool was diluted (i.e., conditioned) to a bulk concentration of about 150 g/L in 0.02 M histidine, 0.2 M arginine-HCl, 0.04% polysorbate-20, pH 6 (final formulation). During the conditioning steps the temperature of the bulk was allowed to return to ambient temperature. After conditioning, the formulated bulk was again recovered through a 0.22 micrometers sterile filter.

The UF/DF system can be regenerated with 0.1 N sodium hydroxide and sanitized with 1.4% Minncare.® When not in use the system can be stored in 0.1N aqueous sodium hydroxide. The UF/DF membranes can be stored, for example, in a 0.1% Roccal®/20% glycerol-water solution between campaigns.

General Ultrafiltration/Diafiltration Process Procedures

Operating Parameters: Feed flow rate at 0.5 L/min/ft². A constant retentate pressure (e.g., 10 psig) control was used for cleaning and pre-use equilibration, whereas $C_{wall}$, constant retentate pressure or constant TMP was used for processing.

Pre-Use Equilibration: The following preparations were accomplished on cleaned Pellicon-2 cassette membranes prior to use to assure the membranes were properly equilibrated.

| Volume (L/ft²) | Solution (room temp) | Mode |
|---|---|---|
| — | — | SPFO |
| 1.0 | WFI | SPFO |
| 1.0 | DF buffer | SPFO |
| 0.5 | DF Buffer | TRFO, 10 minutes |
| — | — | SPFO |

Process Use: The following was performed on the resulting initial anion-exchange pool (Q-pool) obtained from a preceding separation step, for example, a Q-Sepharose chromatography step:

a first ultrafiltering or first ultrafiltration (UF1) to a concentration from about 5 g/L to a concentration for diafiltration ($C_{DF}$);

diafiltering or diafiltration (DF1) with four (4) diafiltration volumes (DV) with the DF buffer;

continued diafiltering (DF2) with four (4) diafiltration volumes (DV) of DF buffer;

a second ultrafiltering or second ultrafiltration (UF2) to a final concentration ($C_{Final}$); and optional product recovery.

The foregoing steps were typically accomplished at low dP Recycle (mix), for example, 15 min.

Post-Use Cleanout: The following tabulated sequence and conditions were used for cleanout on the Pellicon-2 cassette membranes immediately following use.

| Volume (L/ft²) | Solution (room temp) | Mode |
|---|---|---|
| 1.0 | 0.1N NaOH | SPFO |
| 0.5 | 0.1N NaOH | TRFO, 30 minutes |
| — | — | SPFO |
| 1.0 | WFI | SPFO |
| 0.5 | 300 ppm Minncare ® | TRFO, 30 minutes |
| — | — | SPFO |
| 1.0 | WFI | SPFO |
| — | — | Integrity Test @ 30 psig |
| 0.5 | 0.1N NaOH | TRFO, 15 minutes storage |

Definitions for Modes of Operation in TFF

Single Pass with Filtrate Open (SPFO). The retentate and filtrate are directed to drain. Filtrate valve open.

Total Recycle with Filtrate Open (TRFO). The retentate and filtrate are directed to recycle vessel. Filtrate valve open.

Fed-Batch Ultrafiltration (FB-UF). The retentate is directed to the recycle tank, the filtrate directed to drain, and the incoming pool transferred into the recycle tank.

Batch Ultrafiltration (B-UF). The retentate is directed to the recycle tank and the filtrate is directed to drain.

Diafiltration (DF). The retentate is directed to the recycle tank, the filtrate is directed to drain, and the diafiltration buffer is transferred into recycle tank.

dP refers to differential pressure.

Product Transfer. The ultrafilter membrane unit and recycle tank are open to the pool tank. The nitrogen overlay pressure is controlled. The pool is transferred first using the recycle pump and then using a manual peristaltic pump.

Feed Transfer. The incoming pool is pumped into the recycle tank.

Total Recycle with Filtrate Closed (TRFC). The retentate is directed to a recycle vessel. Filtrate valve closed.

"Q-pool" refers to the protein pool resulting from, for example, a preceding Q-Sepharose chromatography step which has been conditioned with buffer, also referred to as the "conditioned pool."

WFI refers to water-for-injection.

EXAMPLES

The following examples serve to more fully describe the manner of using the above-described disclosure, as well as to set forth the best modes contemplated for carrying out various aspects of the disclosure. It is understood that these examples in no way serve to limit the true scope of this disclosure, but rather are presented for illustrative purposes.

Example 1

High Concentration Formulation of rhuMAb E25 A pilot scale UF system was used to concentrate/formulate rhuMAb E25 (a recombinant human monoclonal antibody that targets IgE, U.S. Pat. No. 6,172,213). A Millipore Pelicon Ultrafiltration Diafiltration system was assembled with a 5.7-sqft, 10,000-dalton regenerated cellulose composite membrane. The system consisted of a membrane holder, a Waukeskaw Model 6 rotary lobe feed pump, 1½" 316L stainless steel recirculation piping, and a recirculation vessel. Pressure indicators/transmitters (Anderson) were located at the inlet (FEED), outlet (RETENTATE) and permeate (FILTRATE) of the membrane holder. Flow meters (Yokogawa ADMAG) were located at the inlet (FEED) and permeate (FILTRATE) of the membrane holder. A back-pressure regulating valve (Mikroseal) was located at the outlet of the membrane holder to control the retentate pressure and effect the transmembrane pressure (TMP). A 40-liter 316L stainless steel jacketed tank was used for the recirculation vessel. This tank was fitted with a level indicator, top-mounted agitator (Lightnin), vortex breaker and bottom valve (NovAseptic). Temperature control was achieved through the use of temperature modulated glycol fed to the jacket of the tank.

During this run, the feed flow rate was set to a constant rate of 2.85 L/min (0.5 L/min/ft$^2$). During all pre-use and post-use operations the retentate pressure control was set to a constant of 10 psig. During the ultrafiltering and diafiltering operations the system used a $C_{wall}$ control scheme to control the flux through the membrane, see for example R. van Reis, et al., Constant $C_{wall}$ Ultrafiltration Process Control, *J. of Membrane Science,* 130 (1997), 123-140.

Prior to the process, the system storage solution (0.1N NaOH) was flushed in a single pass to drain mode, first with 2 L/ft$^2$ purified water (PW) and then 1 L/ft$^2$ diafiltration buffer (50 mM Histidine/pH 6.0). After the flushes, the system was equilibrated by recirculating 0.5 L/ft$^2$ diafiltration buffer for 10 min. The pH of the recirculated solution was checked to confirm the equilibration. The level in the tank was then reduced to a minimum measurable value to minimize dilution of the incoming protein pool. The protein pool resulting from a preceding Q-Sepharose chromatography step was measured to be 3.2 g E25/L and had a volume of 43.1 L. The protein was in a solution of 25 mM TRIS buffer and about 200 mM NaCl and pH adjusted to 6.2. To begin the run the protein pool was transferred to the recirculation vessel. In the vessel the pool was agitated via the top mounted impeller and the temperature was maintained at ambient (20-25° C.).

During the process the pool was concentrated in UF1 mode to 50 g E25/L (about 2.8 L). At the beginning of diafiltration the temperature set point of the recirculation vessel was increased to 40° C. The increase in temperature and control was affected by flowing warm glycol through the outer jacket of the tank. The pool was then diafiltered with 8 diavolumes of diafiltration buffer. The diafiltration was performed at a constant volume, which was achieved by matching the flow rate of buffered solution being transferred into the recirculation tank to the flow rate of filtrate being removed from the system. At the end of the diafiltration, the pool was further concentrated in UF2 mode. This phase was also performed using an elevated temperature set point of 40° C. The target for this final concentration was 110 g/L. This was achieved without the need to reduce the feed flow rate. Next, a low pressure drop mixing was performed where the feed pump was controlled to maintain a 5-10 psig pressure drop across the feed channel. A sample was pulled from the recirculation tank and a final bulk concentration of approximately 120 g/L was measured. Table 1 summarizes the throughput and flux results of UF1, DF (DF1+DF2), and UF2.

TABLE 1

| Process Phase | Normalized Throughput (g/ft$^2$/hr) | Normalized Flux (LMH/psig) |
| --- | --- | --- |
| UF1 | 13.8 | 4.97 |
| DF | 13.8 | 2.92 |
| UF2 | 181.4 | 1.64 |

Figure 2:
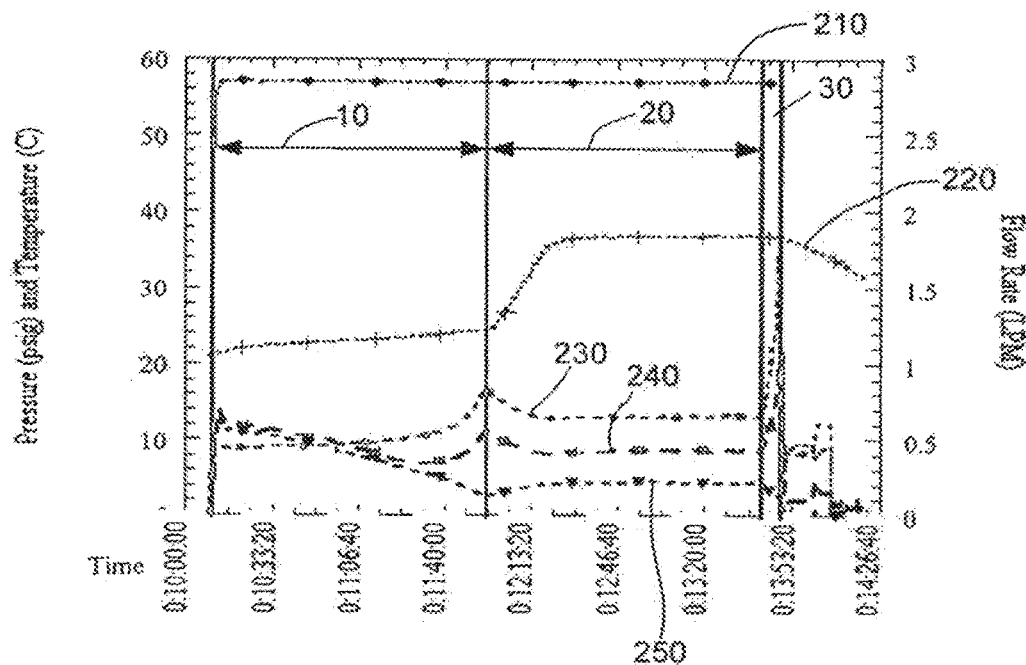
FIGS. 2 through 17 illustrate various observed or measured process values over various phases or mode of the process, in embodiments of the present disclosure.

FIG. 2 shows the observed or measured process values over time for the feed flow rate (210), tank temperature (220), fed dP (230), TMP (240), and filtrate flow rate (250) parameters during the various phases or mode of the process including UF1 (10), DF (20), UF2 (30).

Figure 3:
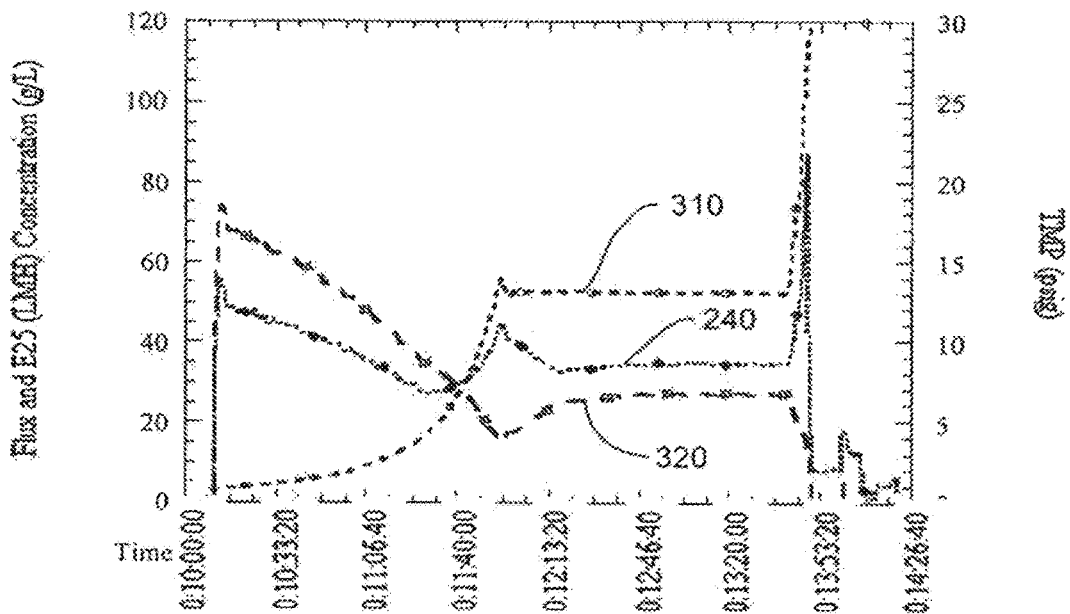
Figure 4:
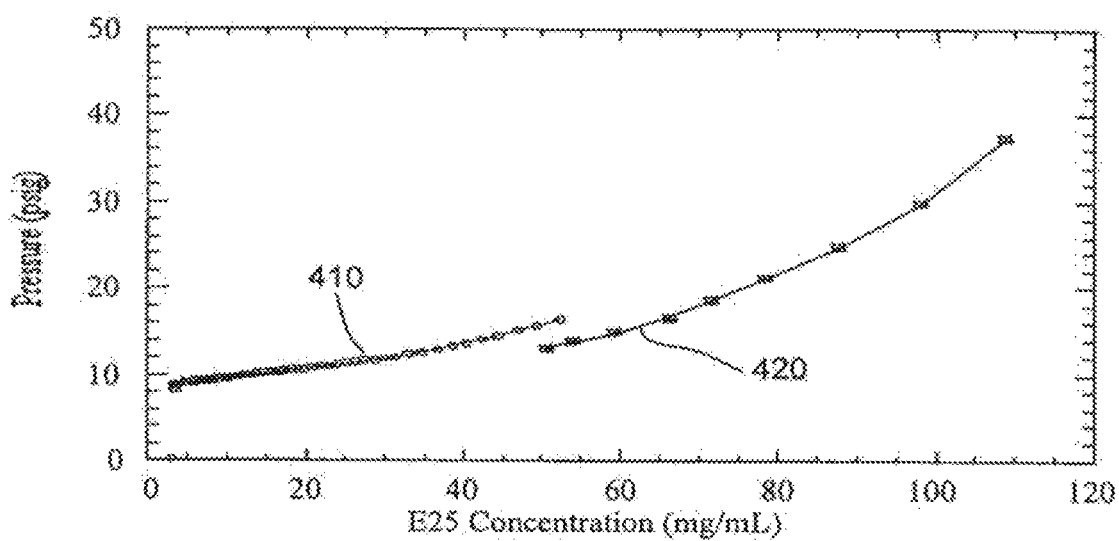

FIG. 3 shows the observed or measured process values over time for the E25 concentration (310), flux (320), and TMP (240), FIG. 4 shows the observed or measured process values over time for pressure drop versus protein concentration observed for UF1 (410) and UF2 (420) at 37° C.

The protein pool was recovered by a series of steps. First the pool in the recirculation tank was pumped from the tank through a Millipac 200, 0.22 microns sterilizing grade filter using the rotary lobe feed pump. Next the protein solution was displaced from the piping and membrane unit with a 5 psig nitrogen gas blow down applied to the highest point on the retentate line. The final phase was a blow down of the tank and feed line, also using the 5 psig nitrogen gas.

The product recovery was believed to be improved compared to Example 1 when conducted at ambient temperature because the elevated temperature used in one or more of the ultrafiltering, diafiltering, or recovery steps reduced viscous effects. For example, when the temperature control was turned off during product recovery, the system slowly cooled during this operation causing difficulties for recovery from the membrane unit. Alternatively, the recovery can be performed first from the membrane holder and then from the recirculation vessel.

To determine the mass of loss during recovery, 1.74 L of DF buffer was added to the system and recirculated for about 5 minutes and recovered using the same sequence as described above. This volume was then analyzed for protein concentration with the other pools. Table 2 summarizes the results.

TABLE 2

|  | Volume (L) | Concentration (g/L) | Mass (g) | Yield or {Loss} (%) |
|---|---|---|---|---|
| Q-Pool | 43.1 | 3.2 | 137.9 | 100 |
| Recovered Pool | 0.99 | 120 | 118.8 | 86.1 |
| Buffer Flush | 1.74 | 9.8 | 17.1 | 12.4 |
| Filtrate | 65.3 | 0.04 | 2.6 | 1.9 |

Post processing, the membrane was regenerated using 0.1N NaOH, 1 L/ft² single pass flush followed by 0.5 L/ft² total recirculation for 30 min. This was followed by 1 L/ft² PW (pure water) flush. This was followed by a total recirculation of 300 ppm Minncare® solution for 30 min. The system was again flushed with 1 L/ft² PW and finally recirculated for 15 min with 0.1N NaOH and stored. The recovered pool was diluted to 80 g E25/L and conditioned into the final formulation of 50 mM histidine/150 mM trehalose/0.02% polysorbate 20/pH 6.0. Product quality was assessed by size exclusion chromatography (SEC) for both the incoming Q-Pool and final recovered bulk. This data is summarized in Table 3.

TABLE 3

| Pool | SEC Results (% monomer) |
|---|---|
| Q-Pool | 99.8 |
| Final Bulk | 99.8 |

Comparative Example 2

High concentration Formulation of rhuMAb E25 at Ambient Temperature Example 1 was accomplished with the following exceptions. Prior to the process, the system storage solution (0.1N NaOH), was flushed in a single pass to drain mode first with 2 L/ft² purified water (PW) and then 1 L/ft² diafiltration buffer (20 mM histidine/pH 6.0). After the flushes the system was equilibrated by recirculating 0.5 L/ft² diafiltration buffer for 10 min. The pH of the recirculated solution was checked to confirm the equilibration. The level in the tank was then reduced to a minimum measurable value to minimize dilution of the incoming protein pool.

The protein pool resulting from the preceding Q-Sepharose chromatography step was measured to be 3.3 g E25/L and had a volume of 33.3 L. The protein was in a solution of 25 mM TRIS buffer and about 200 mM NaCl and pH adjusted to 6.2. To begin the run the protein pool was transferred to the recirculation vessel. In the vessel the pool was agitated via the top mounted impeller and the temperature was maintained at ambient (20-25° C.). During the process the pool was concentrated down in UF1 mode to 50 g E25/L (about 2.2 L). The pool was then diafiltered with 8 diavolumes of diafiltration buffer. The diafiltration was performed at a constant volume, which volume was achieved by matching the flow rate of buffered being transferred into the recirculation tank to the flow rate of filtrate being removed from the system. The diafiltration was also performed at ambient temperature. At the end of the diafiltration, the pool was further concentrated in UF2 mode. The target for this final concentration was 110 g/L. However, due to a high pressure drop across the feed channel, this concentration was not achieved. In an attempt to achieve this concentration the feed flow rate was reduced to 1.4 L/min at a bulk concentration of about 80 g E25/L because the pressure drop across the feed channel had reached 50 psig. UF2 was continued until a high pressure drop of 50 psig again was reached and the process was stopped. Next, a low pressure drop mixing was attempted where the feed pump was used to maintain a 5 psig pressure drop across the feed channel. Again, the viscous nature of the protein solution made it difficult to achieve since the rotary lobe pump reached excess pressures. A sample was pulled from the recirculation tank and a final bulk concentration of approximately 104 g/L was measured. Table 4 summarizes throughput and flux measured during the UF1, DF (DF1+DF2), and UF2 phases.

TABLE 4

| Process Phase | Normalized Throughout (g/ft²/hr) | Normalized Flux (LMH/psig) |
|---|---|---|
| UF1 | 14.5 | 5.31 |
| DF | 9.5 | 1.47 |
| UF2 | 144.6 | 0.78 |

Figure 5:
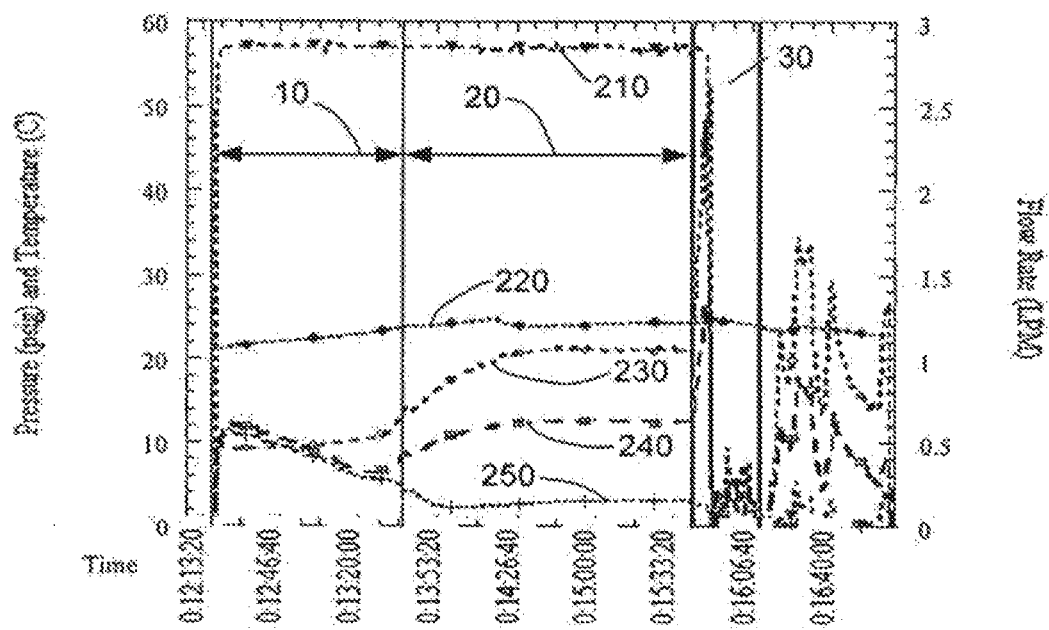

FIG. 5 shows the observed or measured process values over time for the feed flow rate (210), tank temperature (220), fed dP (230), TMP (240), and filtrate flow rate (250) parameters during the various phases or mode of the process including UF1 (10), DF (20), UF2 (30).

Figure 6:
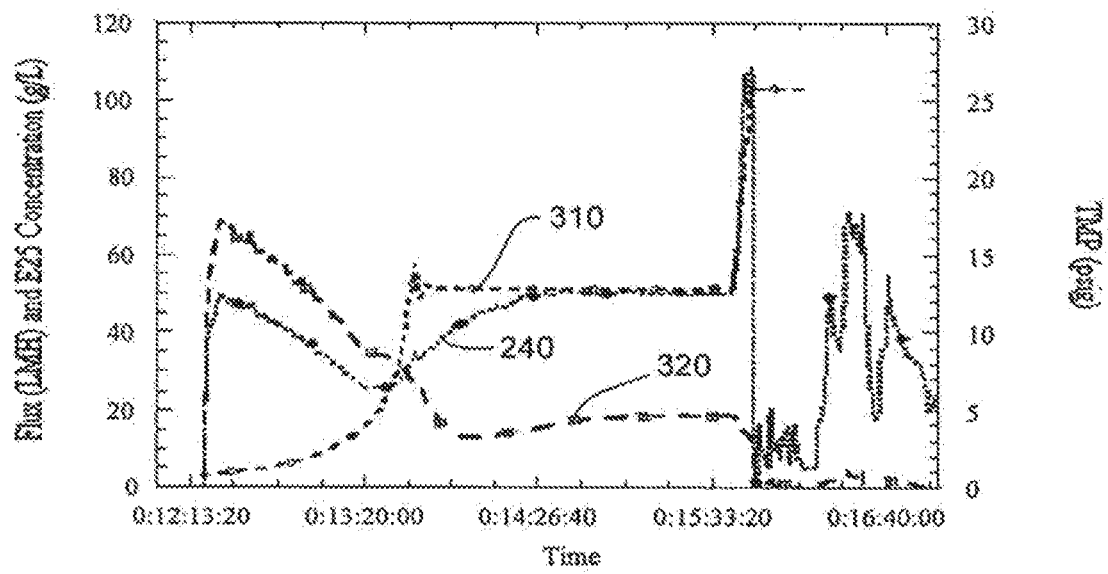

FIG. 6 shows the observed or measured process values over time for the E25 concentration (310), flux (320), and TMP (240).

Figure 7:
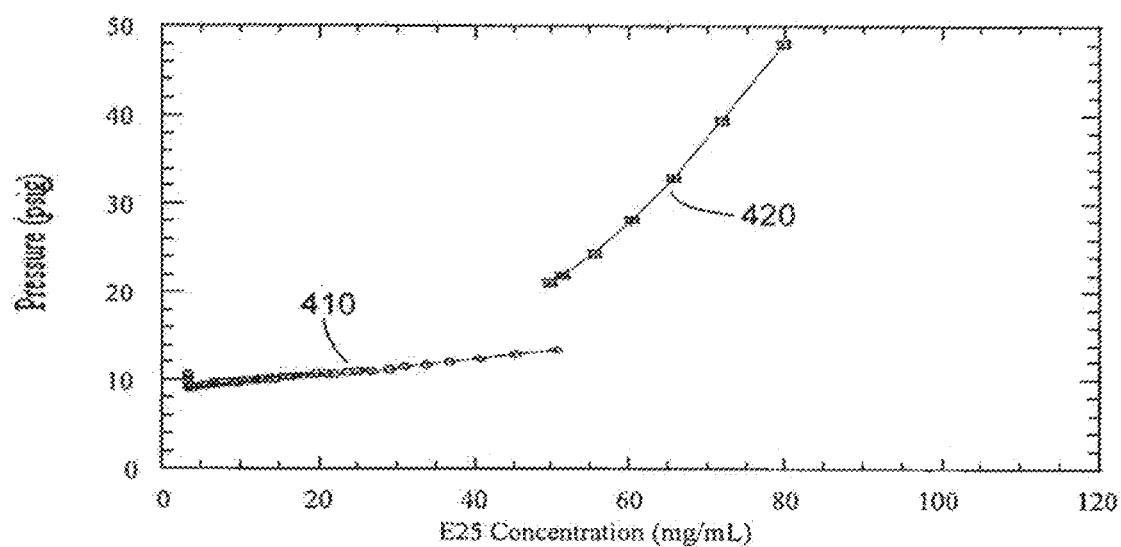

FIG. 7 shows the observed or measured process values over time for pressure drop versus protein concentration observed for UF1 (410) and UF2 (420) at 24° C.

The protein pool was recovered in steps. First, the pool in the recirculation tank was pumped from the tank through a Millipac 200, 0.22 microns sterilizing grade filter using the rotary lobe feed pump. Next the protein solution was displaced from the piping and membrane unit with a 5 psig nitrogen gas blow down applied to the highest point on the retentate line. The product recovery from this was very poor due to the viscous nature of the solution. The final phase was a blow down of the tank and feed line, also using the 5 psig nitrogen gas.

To determine the mass of loss during recovery, 1.85 L of DF buffer was added to the system and recirculated for about 5 minutes and recovered using the sequence of Example 1. This volume was then analyzed for protein concentration with the other pools. Table 5 summarizes the results.

TABLE 5

|  | Volume (L) | Concentration (g/L) | Mass (g) | Yield or {Loss} (%) |
|---|---|---|---|---|
| Q-Pool | 33.3 | 3.3 | 109.9 | 100 |
| Recovered Pool | 0.77 | 104.4 | 80.4 | 73.1 |
| Buffer Flush | 1.85 | 14.7 | 27.2 | 24.7 |
| Filtrate | 52.2 | 0.03 | 1.6 | 1.5 |

Post process, the membrane was regenerated using 0.1N NaOH, 1 L/ft² single pass flush, followed by 0.5 L/ft² total recirculation for 30 min. This was followed by 1 L/ft2 PW flush. This was followed by a total recirculation of 300 ppm Minncare® solution for 30 min. The system was again flushed with 1 L/ft² PW and finally recirculated for 15 min with 0.1N NaOH and stored. The recovered pool was diluted to 80 g E25/L and conditioned into the final formulation of 20 mM histidine/250 mM sucrose/0.02% polysorbate 20/pH 6.0. Product quality was assessed by size exclusion chromatography (SEC) for both the incoming Q-Pool and final recovered bulk. This data is summarized in Table 6.

TABLE 6

| Pool | SEC Results (% monomer) |
|---|---|
| Q-Pool | 99.8 |
| Final Bulk | 99.8 |

Example 3

High Concentration Formulation of rhuMAb E26 with Initial Fed-Batch Mode Example 1 was repeated with the following exceptions. The concentrate/formula was rhuMAb E26 (a recombinant human monoclonal antibody that targets IgE). The products from this example were used in toxicology assessment. The Millipore Pelicon Ultrafiltration/Diafiltration system was assembled with a 11.4-sqft 30,000-Dalton regenerated cellulose composite membrane. The feed flow rate was set to a constant rate of 5.0 L/min (0.44 L/min/ft$^2$). During the ultrafiltration and diafiltration operations the retentate pressure was maintained between about 6-8 psig. The protein pool resulting from the preceding Q-Sepharose chromatography step was measured to be 6.7 g E26/L and had a volume of 59.3 L.

Because the incoming pool was larger then the recirculation vessel, the UF1 process began in fed-batch mode. In this mode, Q-Pool was added to the recirculation vessel at approximately the same rate as filtrate passes through the TFF membrane to drain. After the remaining Q-Pool had transferred to the recirculation vessel, the UF1 process continued in batch mode. During the UF1 the pool was concentrated to 50 g E26/L (about 7.9 L). At the beginning of diafiltration the temperature set point of the recirculation vessel was increased to 40° C. The increase in temperature and control was affected by flowing warm glycol through the outer jacket of the tank. The pool was then diafiltered with 8 diavolumes of diafiltration buffer. The diafiltration was performed at a constant volume which was achieved by matching the flow rate of buffered being transferred into the recirculation tank to the flow rate of filtrate being removed from the system. At the end of the diafiltration, the pool was further concentrated in UF2 mode to a final concentration of 109 g E26/L (3.6 L). This phase was also performed using an elevated temperature set point of 40° C. Next a low pressure drop mixing was performed where the feed pump was controlled to maintain a 5-10 psig pressure drop across the feed channel. Table 7 summarizes the throughput and flux results of UF1, DF (DF1+DF2), and UF2.

TABLE 7

| Process Phase | Normalized throughput (g/ft$^2$/hr) | Normalized Flux (LMH/psig) |
|---|---|---|
| UF1 | 26.1 | 3.71 |
| DF | 19.2 | 2.34 |
| UF2 | 174.2 | 1.80 |

Figure 8:
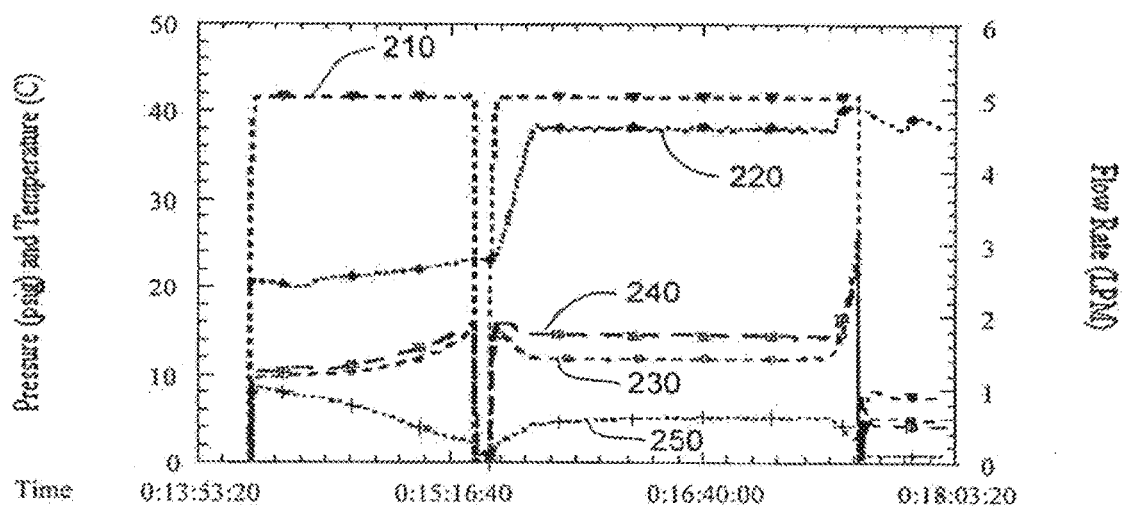

FIG. 8 shows the observed or measured process values over time for the feed flow rate (210), tank temperature (220), fed dP (230), TMP (240), and filtrate flow rate (250).

Figure 9:
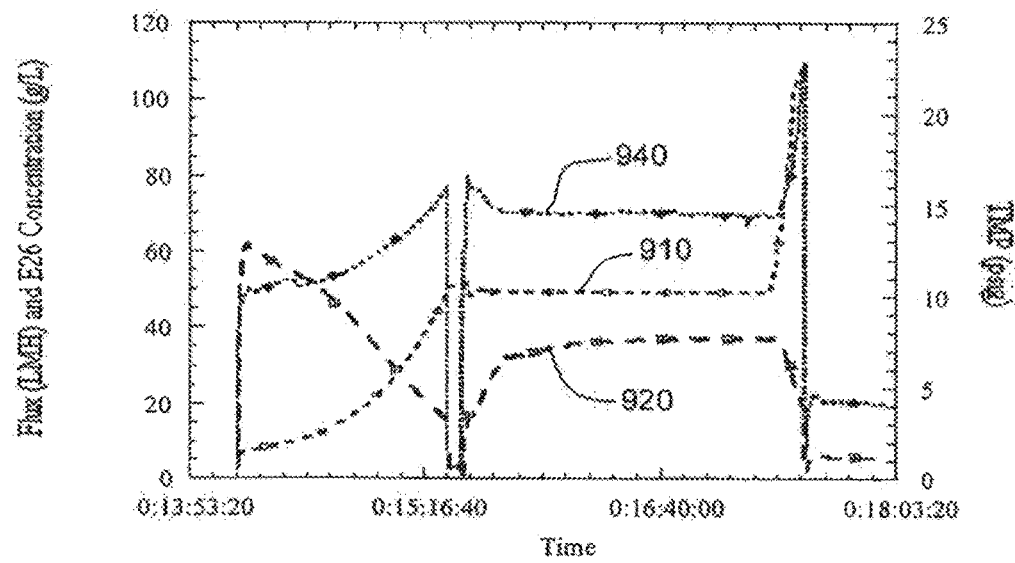

FIG. 9 shows the observed or measured process values over time for the E26 concentration (910), flux (920), and TMP (940).

Figure 10:
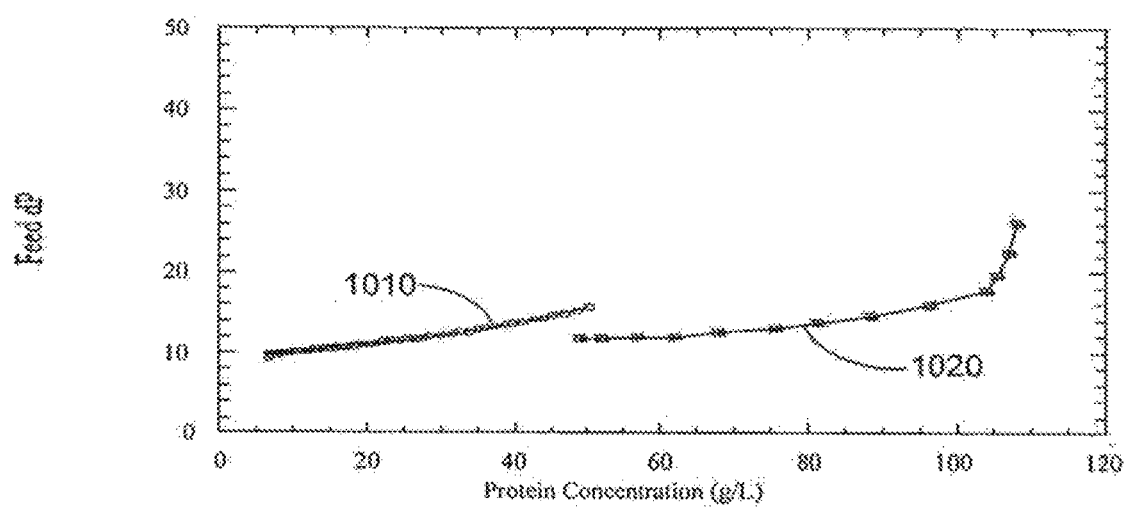

FIG. 10 shows the observed or measured process values over time for pressure drop versus protein concentration observed for UF1 (1010) and UF2 (1020).

Just prior to product recovery, a 10 mL sample was analyzed for detection and a titer of bioburden. A typical reject limit is 1,000 Colony Forming Units (CFU) per mL. The results of this test were 1.8 CFU/mL, a suitable value at this step and well below the reject limit. To determine the mass of loss during recovery, 908.1 mL of DF buffer was added to the system and recirculated for about 5 minutes and recovered using the same sequence described above. This volume was then analyzed for protein concentration with the other pools. Table 8 summarizes the results.

TABLE 8

| | Volume (L) | Concentration (g/L) | Mass (g) | Yield or {Loss} (%) |
|---|---|---|---|---|
| Q-Pool | 59.3 | 6.7 | 397.3 | 100 |
| Recovered Pool | 3.41 | 109.1 | 372.0 | 93.6 |
| Buffer Flush | 0.908 | 20.4 | 18.5 | 4.7 |
| Filtrate | 120 | n/d | n/d | n/d |

The recovered pool was diluted to 80 g E26/L and conditioned into the final formulation of 50 mM histidine/150 mm trehalose/0.02% polysorbate 20/pH 6.0. Product quality was assessed by size exclusion chromatography (SEC) for the incoming Q-Pool, the retentate pool after UF1, the retentate pool after DF, and final recovered bulk. This data is summarized in Table 9.

TABLE 9

| Pool | SEC Results (% monomer) |
|---|---|
| Q-Pool | 99.8 |
| End of UF1 | 99.8 |
| End of DF | 99.8 |
| Final Bulk | 99.8 |

Example 4

High Concentration Formulation of rhuMAb E26 for Toxicology Evaluation-Comparison of 10 kD and 30 kD Example 3 was repeated with the following exceptions. Two pilot scale UF systems were used to concentrate/formulate rhuMAb E26. Two Millipore Pelican Ultrafiltration Diafiltration systems were assembled with a 11.4-sqft, regenerated cellulose composite membrane, one with 10,000-Dalton pore size and the other a 30,000-Dalton pore size. The retentate pressures were maintained at about 6-9 psig.

10 kD Process

The protein pool resulting from the preceding Q-Sepharose chromatography step was measured to be 5.85 g E26/L and had a volume of 62.4 L. During the UF1, the pool was concentrated to 50 g E26/L (about 7.3 L). At the end of the diafiltration, the pool was further concentrated in UF2 mode to a final concentration of 107.5 g E26/L (3.4 L). Table 10 summarizes the throughput and flux results of UF1, DF, and UF2.

TABLE 10

| Process Phase | Normalized throughput (g/ft²/hr) | Normalized Flux (LMH/psig) |
|---|---|---|
| UF1 | 21.8 | 3.6 |
| DF | 15.9 | 2.6 |
| UF2 | 137.4 | 1.93 |

To determine the mass of loss during recovery, 987 mL of DF buffer was added to the system and recirculated for about 5 minutes and recovered using the same sequence described above. This volume was then analyzed for protein concentration with the other pools. Table 11 summarizes the results.

TABLE 11

| | Volume (L) | Concentration (g/L) | Mass (g) | Yield or {Loss} (%) |
|---|---|---|---|---|
| Q-Pool | 62.4 | 5.85 | 365.4 | 100 |
| Recovered Pool | 3.38 | 107.5 | 361.7 | 98.9 |
| Buffer Flush | 0.987 | 19.9 | 19.6 | 5.4 |
| Filtrate | 125 | n/d | n/d | n/d |

Figure 11:
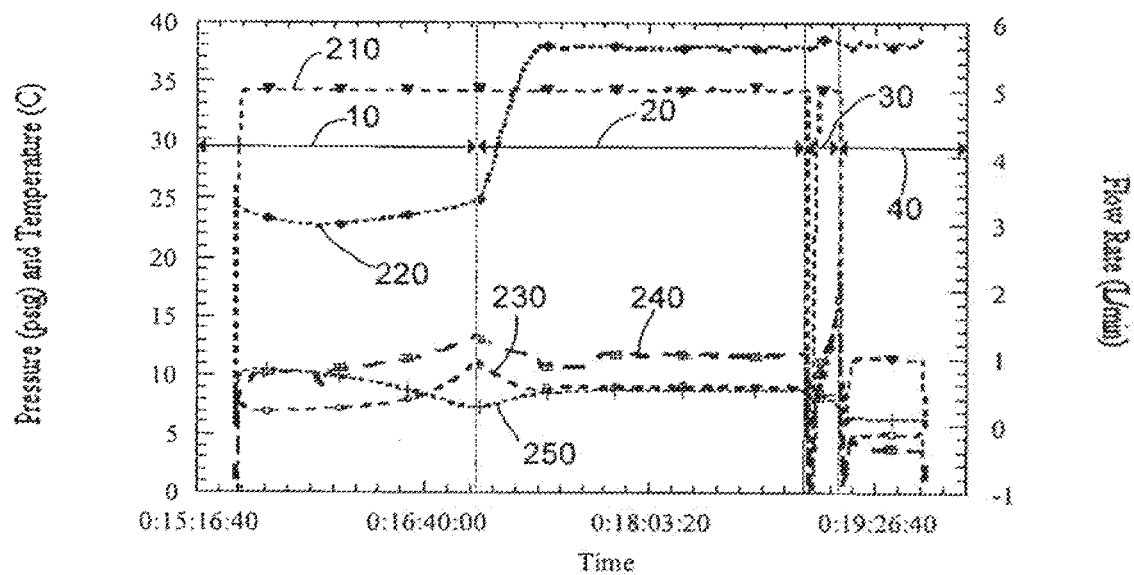

FIG. 11 shows the observed or measured process values over time for the feed flow rate (210), tank temperature (220), fed dP (230), TMP (240), and filtrate flow rate (250) over the various phases or mode of the process including UF1 (10), DF (20), UF2 (30), and low dP (40), for the 10 kD process.

Figure 12:
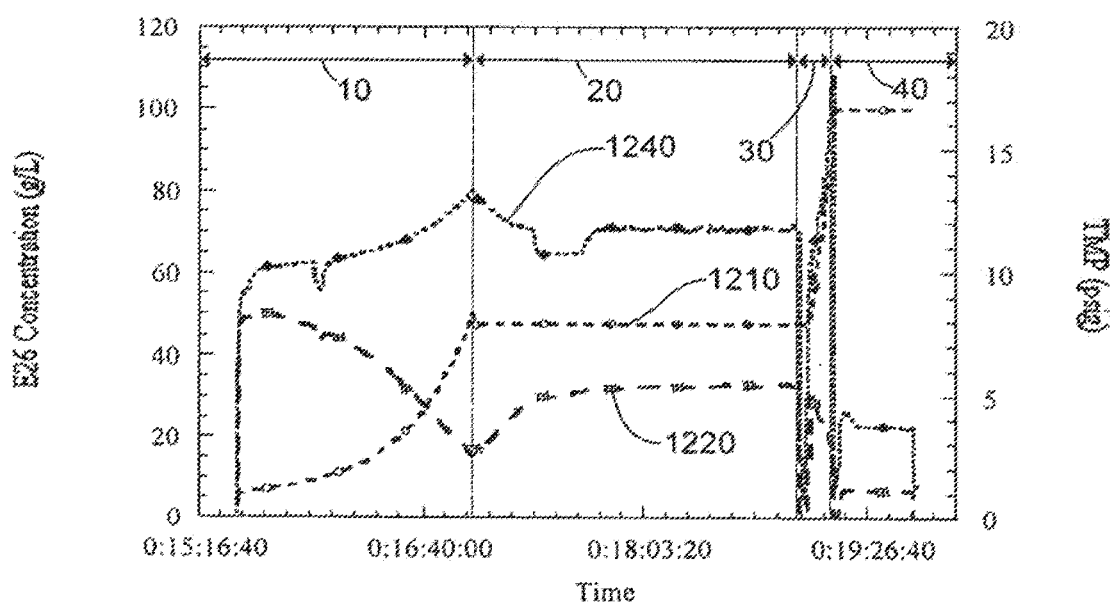

FIG. 12 shows the observed or measured process values over time for the E26 concentration (1210), flux (1220), and TMP (1240) over the various phases or mode of the process including UF1 (10), DF (20), UF2 (30), and low dP (40), for the 10 kD process.

Figure 13:
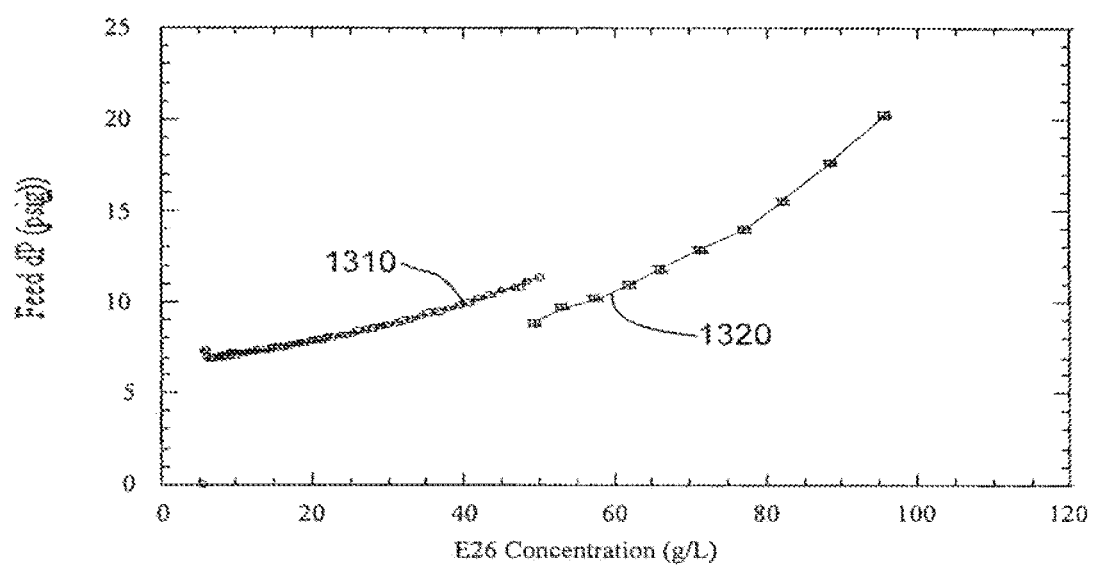

FIG. 13 shows the observed or measured process values over time for pressure drop versus protein concentration observed for UF1 (1310) and UF2 (1320) for the 10 kD process.

30 kD Process

The protein pool resulting from the preceding Q-Sepharose chromatography step was measured to be 5.85 g E26/L and had a volume of 64.5 L. During the UF1 the initial pool was concentrated to 50 g E26/L (about 7.5 L). At the end of the diafiltration, the pool was further concentrated in UF2 mode to a final concentration of 117.5 g E26/L (3.2 L). Table 12 summarizes the throughput and flux results of UF1, DF, and UF2.

TABLE 12

| Process Phase | Normalized throughput (g/ft²/hr) | Normalized Flux (LMH/psig) |
|---|---|---|
| UF1 | 25.5 | 4.01 |
| DF | 17.6 | 2.39 |
| UF2 | 180.5 | 1.57 |

To determine the mass of loss during recovery, 918 mL of DF buffer was added to the system and recirculated for about 5 minutes and recovered using the same sequence described above. The recovered pool was diluted to 80 g E26/L and conditioned into the final formulation of 50 mM histidine/150 mM trehalose/0.02% polysorbate 20/pH 6.0. Table 13 summarizes the results.

TABLE 13

| | Volume (L) | Concentration (g/L) | Mass (g) | Yield or {Loss} (%) |
|---|---|---|---|---|
| Q-Pool | 64.5 | 5.85 | 377.3 | 100 |
| Recovered Pool | 3.20 | 117.5 | 376.0 | 99.6 |
| Buffer Flush | 0.918 | 22.7 | 20.8 | 5.5 |
| Filtrate | 125 | n/d | n/d | n/d |

Figure 14:
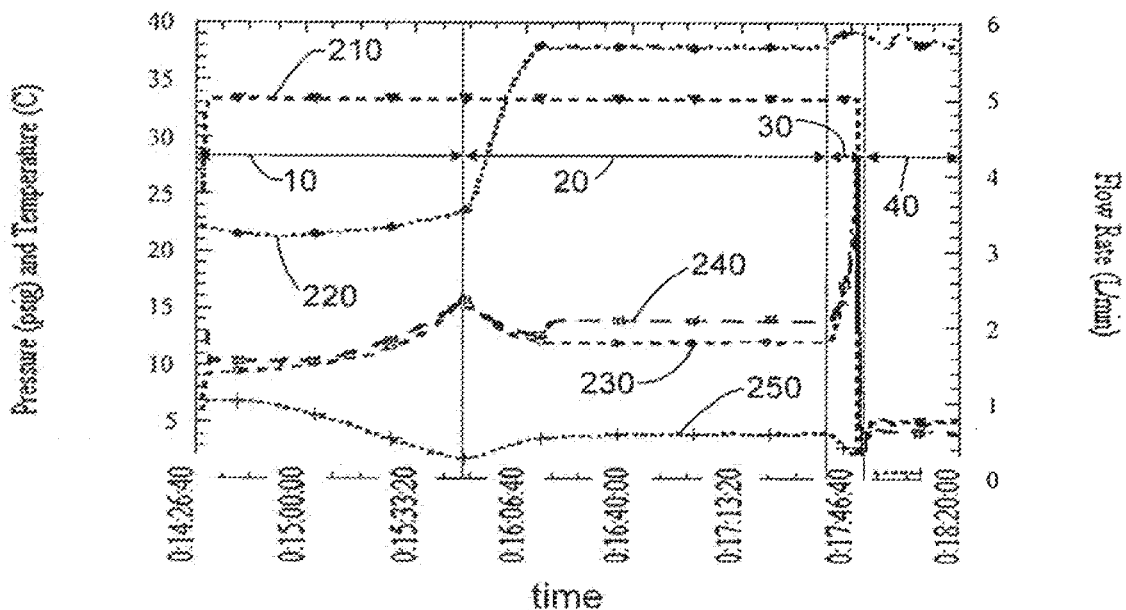

FIG. 14 shows the observed or measured process values over time for the feed flow rate (210), tank temperature (220), fed dP (230), TMP (240), and filtrate flow rate (250) over the various phases or mode of the process including UF1 (10), DF (20), UF2 (30), and low dP (40), for the 30 kD process.

Figure 15:
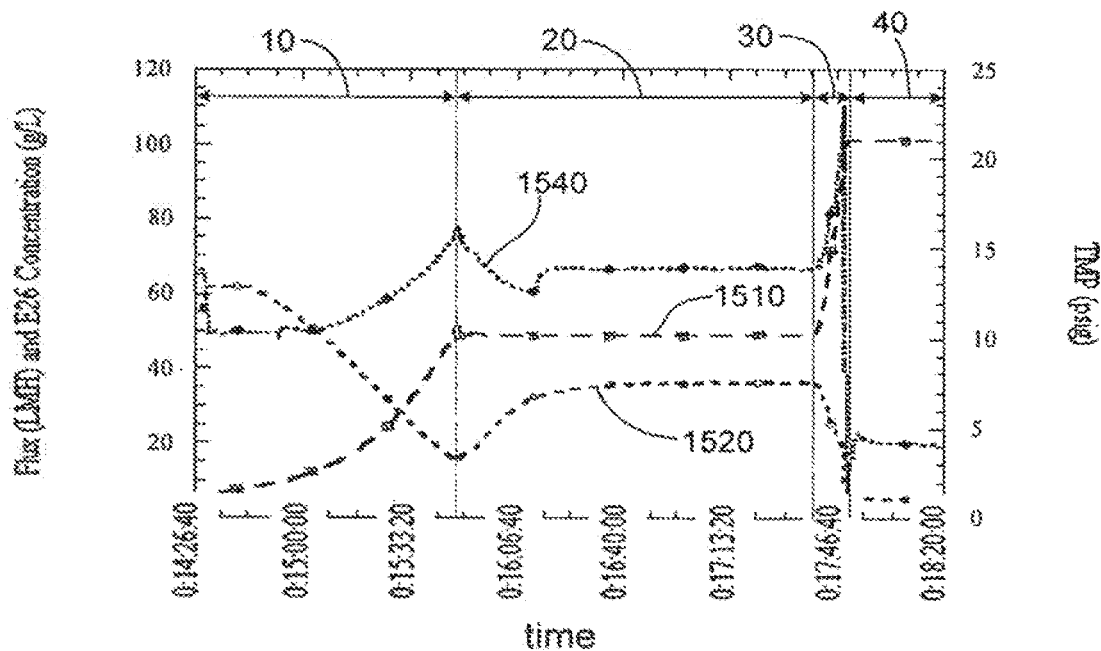

FIG. 15 shows the observed or measured process values over time for the E26 concentration (1510), flux (1520), and TMP (1540) over the various phases or mode of the process including UF1 (10), DF (20), UF2 (30), and low dP (40), for the 30 kD process.

Figure 16:
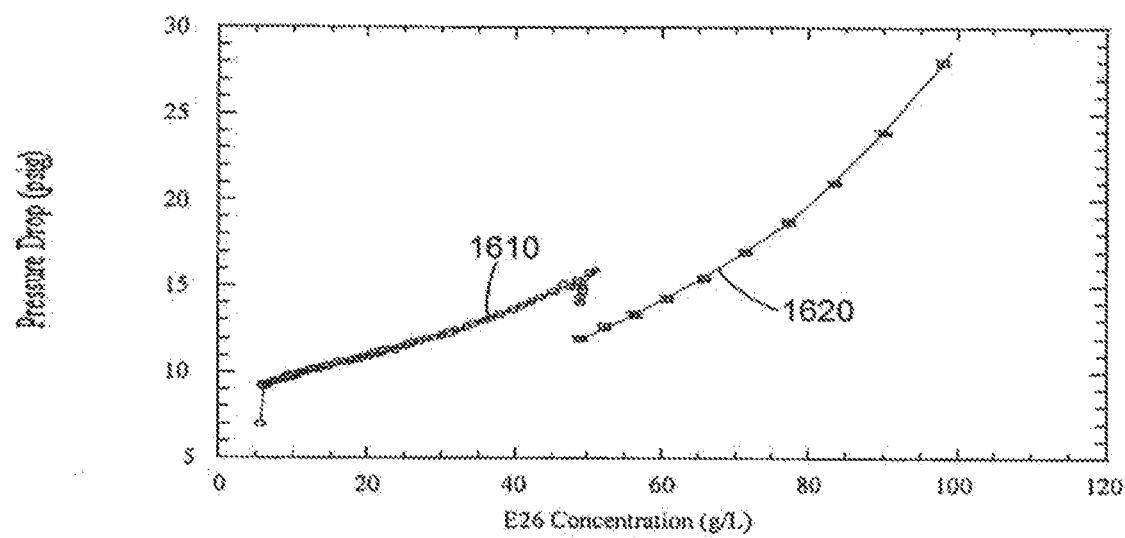

FIG. 16 shows the observed or measured process values over time for pressure drop versus protein concentration observed for UF1 (1610) and UF2 (1620) for the 30 kD process.

Example 5

Liquid rhuMAb E25 Scale Up Example 1 was repeated with the following exceptions. A production scale UF system was used to concentrate/formulate a liquid rhuMAb E25 (a recombinant human monoclonal antibody that targets IgE). The product can be used in therapeutic application and human bio-equivalency trials. The Millipore Pelicon Ultrafiltration/Diafiltration systems were assembled with a 226-sqft regenerated cellulose composite membrane, with a pore size of 30,000-Dalton. Each system consisted of a membrane holder, a Viking S3S rotary lobe feed pump, 1½" 316L stainless steel recirculation piping, and a 250-L recirculation vessel.

One 250-liter 316L stainless steel jacketed tank was used for the recirculation vessel. Temperature control to this tank was achieved with a temperature modulated glycol fed to the tank's jacket. The temperature of the glycol fed to the tank jacket was raised or lowered using either steam-fed heat exchanger or cold glycol supply respectively.

For this run, the feed flow rate was set to a constant rate of 114 L/min (0.5 L/min/ft²). The diafiltration buffer (20 mM histidine/200 mM arginine chloride/pH 6.0) was prepared in a separate tank. The temperature of this buffer was set to 45° C. prior to the process. This enabled accurate temperature control throughout the process.

Prior to processing, the system storage solution (0.1N NaOH) was flushed in a single pass to drain mode first with 1 L/ft² water for injection (WFI) and then 1 L/ft² diafiltration buffer. After the flushes, the system was equilibrated by recirculating 0.5 L/ft² diafiltration buffer for 10 min. The pH of the recirculated solution was checked to confirm the equilibration.

The protein pool resulting from the preceding Q-Sepharose chromatography step was measured to be 5.2562 g E25/L and had a volume of 1,141 L. The protein was in a solution of 25 mM TRIS buffer and about 200 mM NaCl and the pH was adjusted to 6.2. Just prior to the run, the temperature set point of this pool was set to 45° C. To begin the run the protein pool was transferred to the recirculation vessel, through a 0.22 microns sterilizing grade filter to a level of about 200 L in the tank. In the vessel the pool was agitated via a top mounted impeller and the temperature was maintained at about (40-50° C.). Because the incoming pool was larger then the recirculation vessel, the UF1 process began in fed-batch mode. In this mode, Q-Pool was added to the recirculation vessel at approximately the same rate as filtrate passes through the TFF membrane to drain. After the remaining Q-Pool was transferred to the recirculation vessel, the UF2 process was continued in batch mode. During the UF1 mode the pool was concentrated to about 30 g E25/L (about 200 L). The pool was then diafiltered with about 8 diavolumes of diafiltration buffer: During diafiltration the temperature was maintained between 40° and 50° C. The diafiltration was performed at a constant volume, which was achieved by matching the flow rate of buffer being transferred into the recirculation tank to the flow rate of filtrate being removed from the system. At the end of the diafiltration, the pool was further concentrated in UF2 mode to a final concentration set point of >170 g E25/L (35 L). This UF2 mode phase was also performed at an elevated temperature set point of 45° C.+/−5° C. Next, a low pressure drop mixing was performed where the feed pump was controlled to maintain a 5-10 psig pressure drop across the feed channel. A sample was pulled and a spec scan was performed to confirm the concentration prior to recovery. The concentration of this sample was 219 g E25/L. Table 14 summarizes throughput and flux measured during the UF1, DF (DF1+D2), and UF2 phases.

TABLE 14

| Process Phase | Normalized throughput (g/ft²/hr) | Normalized Flux (LMH/psig) |
|---|---|---|
| UF1 | 43.8 | 3.34 |
| DF | 25.9 | 2.46 |
| UF2 | 78.9 | 0.66 |

Just prior to product recovery, a 30 mL sample was pulled and submitted for detection and titer of bioburden. The result was <0.13 CFU/mL. The protein pool was recovered by a series of steps. First, the product was displaced from the membrane in a single pass mode using 5 L of DF buffer added to the retentate line. The product was filtered into a recovery tank through a 7.4 ft², 0.22 microns sterilizing-grade guard filter followed by a 2 ft², 0.22 microns sterilizing-grade final filter. The pool in the recirculation tank was then pumped from the tank using the rotary lobe feed pump. Next the residual protein solution was displaced from tank and feed line with a 5 psig nitrogen gas blow down. The final phase was a blow down of the membrane unit, which now contained mostly DF buffer from the initial product displacement. This phase also used the 5 psig nitrogen gas applied to the highest point on the retentate line. The recovered pool was diluted first to about 153 g E25/L using DF buffer. Finally, the pool was conditioned into the final formulation of 20 mM histidine/200 mM arginine-HCl/0.04% polysorbate 20/pH 6.0. The volumes of the recovered pool, diluted pool, and conditioned pool (Q-pool) were then each analyzed for protein concentration. Table 15 summarizes the results.

TABLE 15

| | Volume (L) | Concentration (g/L) | Mass (g) | Yield or {Loss} (%) |
|---|---|---|---|---|
| Q-Pool | 1,141 | 5.2562 | 5,997.3 | 100 |
| Recovered Pool | 35.0 | 170.0 | 5,950.0 | 99.2 |
| Diluted Pool | 39.0 | 147.0 | 5,726 | 95.5 |

Figure 17:
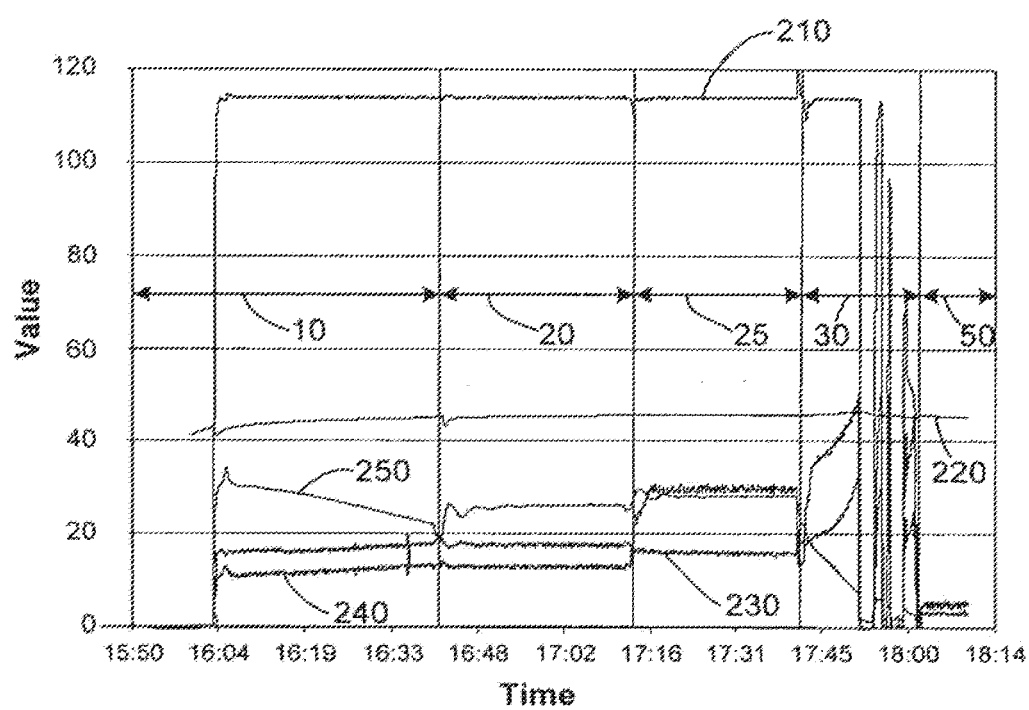

FIG. 17 shows feed flow rate (210), tank temperature (220), fed dP (230), TMP (240), and filtrate flow rate (250) parameters during the various phases or mode of the process including UF1 (10), DF1 (20), DF2 (25), UF2 (30), and low dP (50).

Example 6

Liquid rhuMAb E25 Preparation Example 5 was repeated with following exceptions. A production scale UF system was used to concentrate/formulate liquid rhuMAb E25 (E25, a recombinant human monoclonal antibody that targets IgE). The Millipore Pelicon Ultrafiltration/Diafiltration systems were assembled with a 226-sqft regenerated cellulose composite membrane, with a pore size of 30,000-dalton. Each system consisted of a membrane holder, a Viking S3S rotary lobe feed pump, 1½" 316L stainless steel recirculation piping, and a 250-L recirculation vessel. One 250-liter 316L stainless steel jacketed tank was used for the recirculation vessel. The feed flow rate was set to a constant rate of 114 L/min (0.5 L/min/ft²). During all pre-use and post-use operations the retentate pressure control was set to a constant of 10 psig. During the ultrafiltration and diafiltration operations the system used the $C_{wall}$ control scheme to control the flux through the membrane. The diafiltration buffer (20 mM Histidine/200 mM arginine chloride/pH 6.0) was prepared in a separate tank. The temperature of this buffer was set to 45° C. prior to the process. This enabled accurate temperature control through the entire process. The protein pool resulting from the preceding Q-Sepharose chromatography step was measured to be 5.5438 g E25/L and had a volume of 1,082 L. The protein was in a solution of 25 mM TRIS buffer and about 200 mM NaCl and pH adjusted to 6.2. Just prior to the run, the temperature set-point of this pool was set to 45° C. To begin the run the protein pool was transferred to the recirculation vessel, through a 0.22 microns sterilizing grade filter to a level of about 200 L in the tank. In the vessel the pool was agitated via the top mounted impeller and the temperature was maintained at ambient (40-50° C.). Because the incoming pool was larger then the recirculation vessel, the UF1 process began in fed-batch mode. In this mode, Q-Pool was added to the recirculation vessel at approximately the same rate as filtrate passes thought the TFF membrane to drain. After the remaining Q-Pool had transferred to the recirculation vessel, the UF1 process continued in batch mode. During the UF1 the pool was concentrated to about 30 g E25/L (about 200 L). The pool was then diafiltered with 8 diavolumes of diafiltration buffer. During diafiltration the temperature was maintained between 40 and 50° C. The diafiltration was performed at a constant volume, which was achieved by matching the flow rate of buffered being transferred into the recirculation tank to the flow rate of filtrate being removed from the system. At the end of the diafiltration, the pool was further concentrated in UF2 mode to a final concentration set-point of greater than 170 g E25/L (35 L). This phase was also performed at an elevated temperature set point of 45° C.+/−5° C. Next, a low pressure drop mixing was performed where the feed pump was controlled to maintain a 5-10 psig pressure drop across the feed channel. A sample was pulled and a spec scan was performed to confirm the concentration prior to recovery. The concentration of this sample was 191 g E25/L and the pool volume was 31.9 L. A graph of the process parameters over time were comparable to those observed and summarized for the above FIG. 17.

TABLE 14

| Process Phase | Normalized throughput (g/ft²/hr) | Normalized Flux (LMH/psig) |
|---|---|---|
| UF1 | 45.1 | 3.21 |
| DF | 25.9 | 2.51 |
| UF2 | 121.4 | 0.79 |

Just prior to product recovery, a 30 mL sample was pulled and analyzed for a titer of bioburden. The results of this test were below the detection limit (<0.13 CFU/mL). The protein pool was recovered by a series of steps. First the product was displaced from the membrane in a single pass mode using 5 L of DF buffer added to the retentate line. The product was filtered into a recovery tank through a 7.4 ft², 0.22 microns sterilizing-grade guard filter followed by a 2 ft², 0.22 microns sterilizing-grade final filter. The pool in the recirculation tank was then pumped from the tank using the rotary lobe feed pump. Next, the residual protein solution was displaced from tank and feed line with a 5 psig nitrogen gas blow down. The final phase was a blow down of the membrane unit, which contained mostly DF buffer from the initial product displacement. This phase also used 5 psig nitrogen gas applied to the highest point on the retentate line. The recovered pool was diluted first to about 153 g E25/L using DF buffer. Finally the pool was conditioned into the final formulation of 20 mM histidine/200 mM arginine-HCl/ 0.04% polysorbate 20/pH 6.0. The volumes of the recovered pool, diluted pool, and conditioned pool were then analyzed for protein concentration. Table 15 summarizes the results. Post process, the membrane was regenerated as described above.

TABLE 15

| | Volume (L) | Concentration (g/L) | Mass (g) | Yield or {Loss} (%) |
|---|---|---|---|---|
| Q-Pool | 1,082 | 5.5438 | 5,998.4 | 100 |
| Recovered Pool | 34.95 | 167.08 | 5,839.8 | 97.4 |
| Diluted Pool | 38.2 | 152.14 | 5,810.3 | 96.7 |

Example 7

Figure 18:
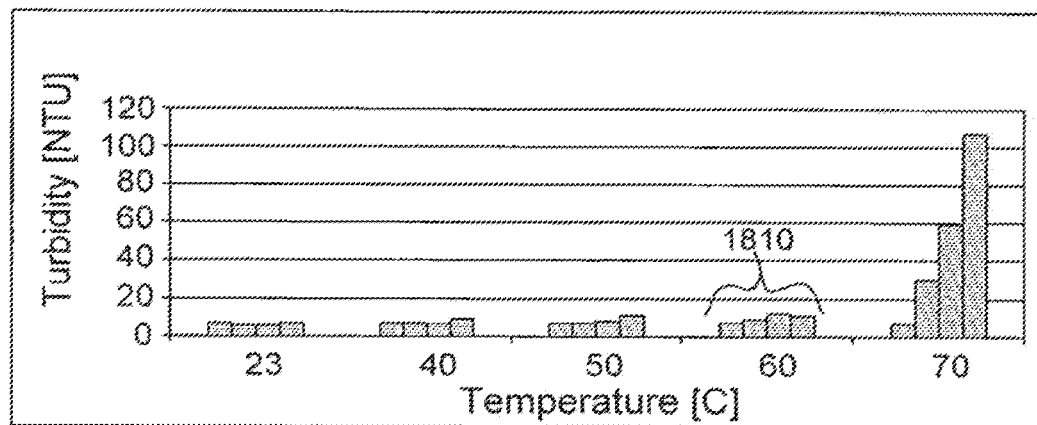
FIGS. 18 and 19 illustrate the effect of elevated temperature on product quality, in embodiments of the present disclosure.
Figure 19:
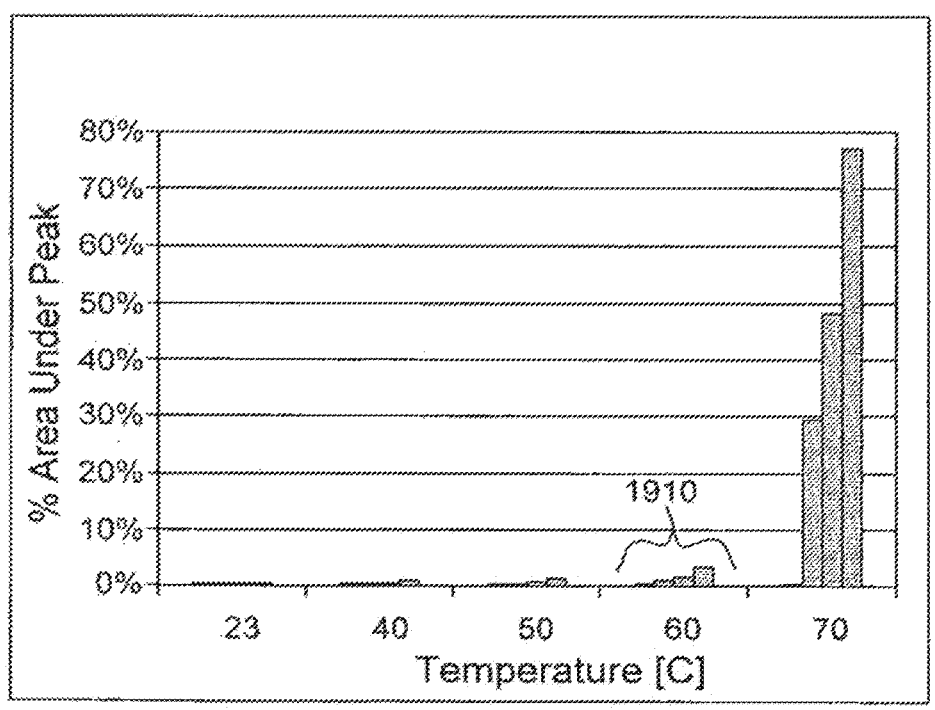

Effect of Elevated Temperature on Product Quality E25 samples at 30 g/L and 150 g/L in histidine and Q buffers were kept a various temperatures for 24 hours. Samples were taken for turbidity measurements and SEC assays. The results of turbidity versus temperature for E25 at 30 g/L in Q buffer are shown in FIG. 18. FIG. 19 shows the amount of soluble aggregate of £25 (150 g/L in 50 mM histidine buffer, pH 6.0) observed over time and at temperatures of 23° C., 40° C., 50° C., 60° C. and 70° C. The four time intervals (time of 0 hours, 4 hours, 7.5 hours, and 24 hours) for each of these temperatures is shown as the cluster of four bars from left to right as 1810 and 1910, in FIGS. 18 and 19. The solution turbidity was essentially unchanged after 24 hours at 60° C. No significant soluble aggregate of E25 was observed below 70° C. suggesting the product samples were substantially stable up to at least 60° C. and at least 24 hours.

Example 8

Figure 20:
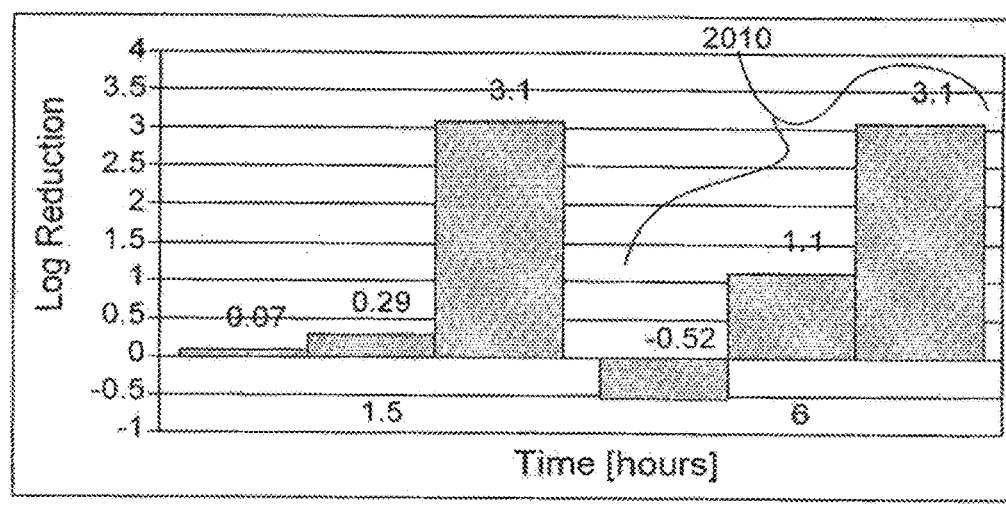
FIGS. 20 and 21 illustrate the effect of elevated temperature on bioburden control, in embodiments of the present disclosure.
Figure 21:
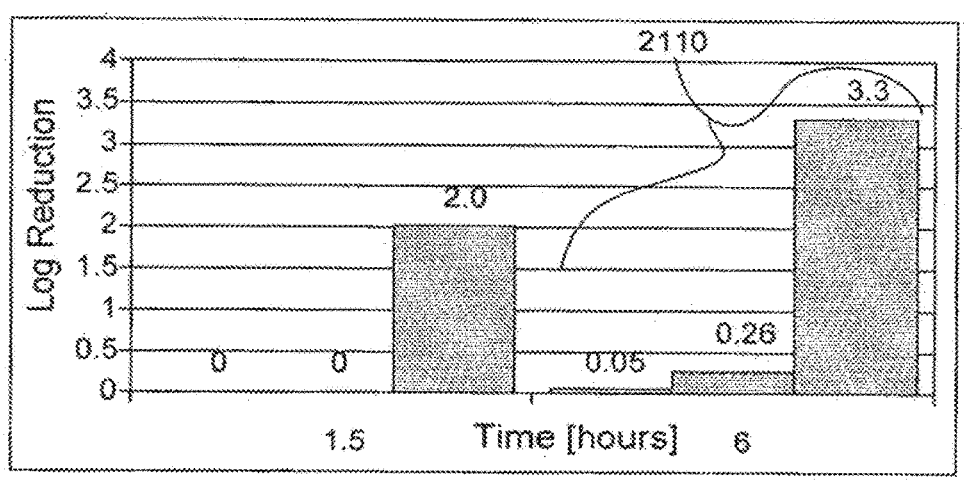

Effect of Elevated Temperature on Bioburden E25 samples at 30 g/L in both arginine and histidine buffers were inoculated with 10³ colony forming units per mL for two challenge organisms: a Gram positive strain (*Staphylococcus aureus*); and one Gram negative strain (*Pseudomonas chlororaphis*). Samples were taken after 1.5 hours and 6 hours. The results shown in the bar charts of FIGS. 20 and 21 indicate that these challenge organisms both decreased with increasing temperature. The three temperature intervals (temp of 25° C., 40° C., and 50° C. hours) for each observed time interval is shown as the cluster of three bars from left to right as 2010 and 2110, in FIGS. 20 and 21. The inoculations shown were conducted in arginine buffer with protein concentrations of 30 g/L.

Example 9

Figure 22:
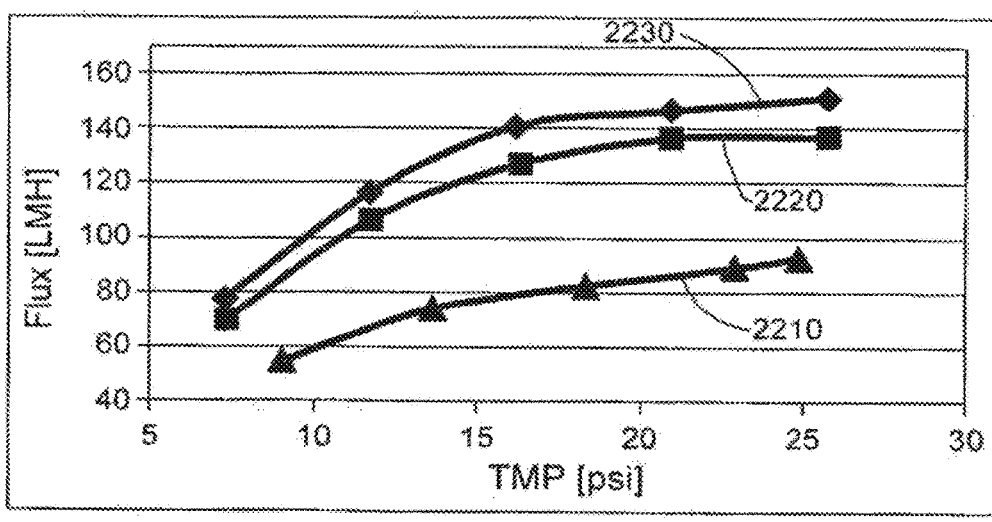
FIG. 22 illustrates the effect of elevated temperature on process flux and process time, in embodiments of the present disclosure.

Effect of Elevated Temperature on Process Flux E25 samples at 10 g/L in 0.2M arginine, 25 mM histidine, pH 6.0 buffer were evaluated for their influence on flux versus transmembrane pressure (TMP). FIG. 22 shows that raising the system temperature also increased the process flux during the UF/DF operations. Flux excursions at various bulk concentrations and three different temperatures of 23° C. (2210), 40° C. (2220), and 46° C. (2230) were performed. The mass transfer coefficient and filtrate flux increased by about 2 to about 3 fold providing considerably reduced process times.

Example 10

High Concentration Formulation of rhuMAb anti-CD20 ("2H7") A pilot scale UF system was used to concentrate and formulate rhuMAb anti-CD20 (2H7; a recombinant human monoclonal antibody). Example 1 was repeated with the following exceptions. The Millipore Pelicon Ultrafiltration/ Diafiltration systems were assembled with a 17.5-sqft, regenerated cellulose composite membrane, with a pore size of 30,000-Dalton. The system consisted of a membrane holder, a Viking S1 L rotary lobe feed pump, 1½" 316 L stainless steel recirculation piping, and a 40-L recirculation vessel. Backpressure regulating valves were H.D. Baumann, Inc. The temperature of the glycol fed the tank jacket was regulated higher or lower as needed using an electric heat exchanger, a cold glycol supply, or both.

Figure 23:
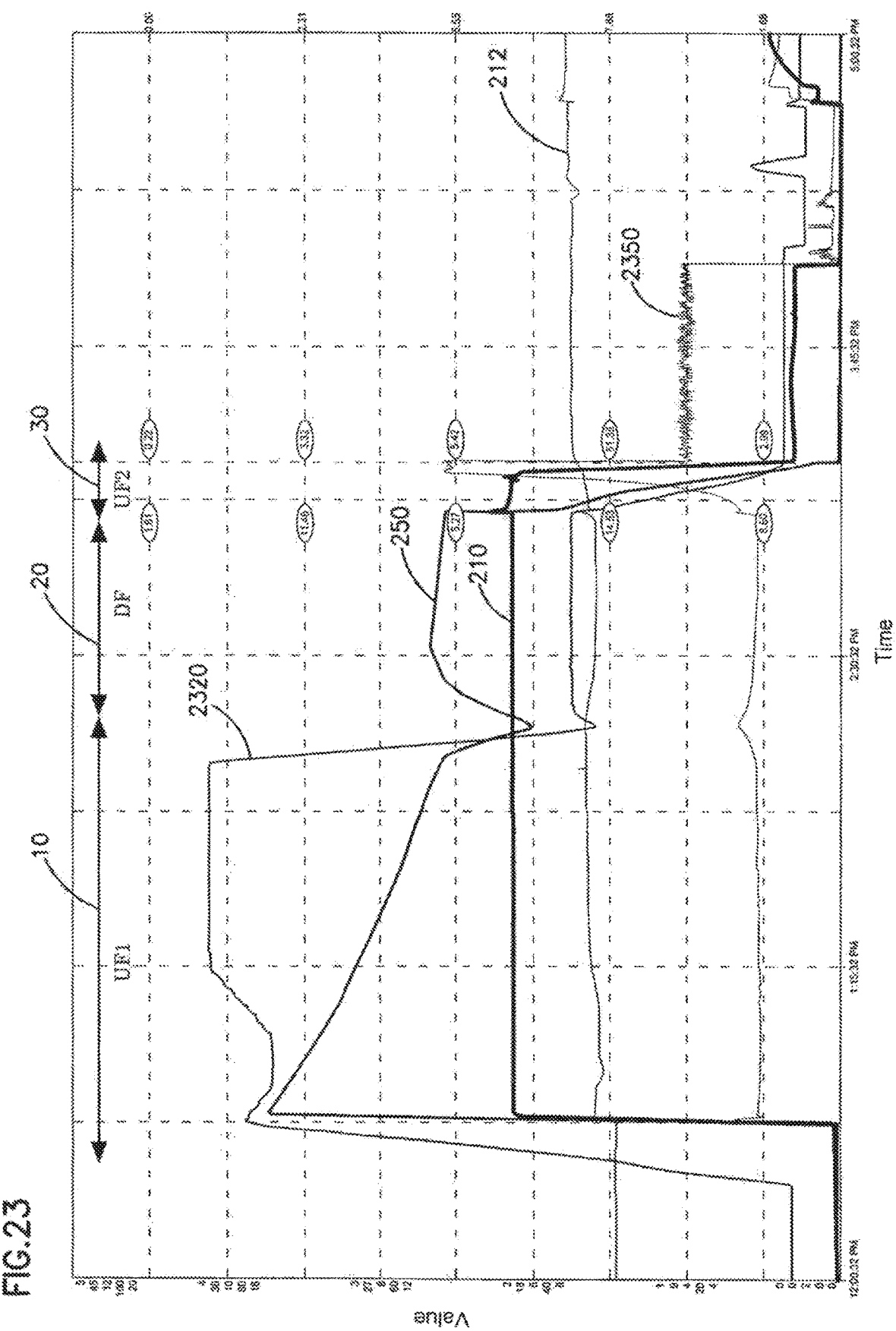
FIGS. 23 through 25 illustrates various observed or measured process values over various phases or mode of the scaled-up process, in embodiments of the present disclosure.

During this run, the feed flow rate was set to a constant rate of 8.5 L/min (approximately 0.5 L/min/ft²). FIG. 23 displays the value trends over time for feed flow rate (210) scaled from 0 to 20, pH (212) scaled from 2 to 12, filtrate flow rate (250) scaled from 0 to 5, recycle tank level (2320) scaled from 0 to 45, and retentate dP (2350) scaled from 0 to 100 during the various phases or mode of the process including UF1 (10), DF1 (20), and UF2 (30).

During the ultrafiltration and diafiltration operations the system used constant retentate pressure followed by a constant feed/retentate delta pressure control scheme to control the flux through the membrane. The diafiltration buffer (30 mM sodium acetate/pH 4.9) was prepared in a separate tank. The temperature of this buffer was set to 45° C. prior to the process for accurate temperature control through the entire process. Prior to processing, the system storage solution (0.1 N NaOH) was flushed in a single pass to drain mode first with 1 L/ft² water for injection (WFI) and then 1 L/ft² diafiltration buffer. After the flushes the system was equilibrated by recirculating 0.5 L/ft² diafiltration buffer for 10 min. The pH of the recirculated solution was checked to confirm the equilibration.

The protein pool resulting from a preceding Q-Sepharose chromatography step was measured to be 2.31 g 2H7/L and had a volume of 356 L. The protein was in a solution of 6 mM HEPES free acid/19 mM HEPES sodium salt and 25 mM sodium acetate that had been pH adjusted to 5.3 with 0.5 M acetic acid. Just prior to the run, the temperature set point of this pool was set to 45° C. To begin the run the protein pool was transferred to the recirculation vessel through a 0.22 microns sterilizing grade filter to a level of about 40 L in the tank. In the vessel the pool was agitated via the top mounted impeller and the temperature was maintained at 40-50° C.

Because the incoming pool was larger then the recirculation vessel, the UF1 process began in fed-batch mode (see FIG. 23). In this mode, Q-Pool was added to the recirculation vessel at approximately the same rate at as filtrate passes thought the TFF membrane to drain. After the remaining Q-Pool has transferred to the recirculation vessel, the UF1 process continued in batch mode. During the UF1 the pool was concentrated to about 50 g 2H7/L (about 16 L). The pool was then diafiltered with 10 diavolumes of diafiltration buffer. During diafiltration the temperature was maintained between 40 and 50° C. The diafiltration was performed at a constant volume, which was achieved by matching the flow rate of buffered being transferred into the recirculation tank to the flow rate of filtrate being removed from the system. At the end of the diafiltration, the pool was further concentrated in UF2 mode to a final concentration target set point of 190 g 2H7/L (4.3 L). See in FIG. 23 the incorporation of constant dP control at 50 psig at the end of this phase. This phase was also performed at an elevated temperature set point of 45° C.+/−5° C. Next, a low pressure drop mixing was performed where the feed pump was controlled to maintain a 20 psig pressure drop across the feed channel. A sample was pulled and a density measurement was performed to confirm the concentration prior to recovery. The concentration of this sample was 189 g 2H7/L. Table 16 summarizes the throughput and flux results.

TABLE 16

| Process Phase | Normalized throughput (g/ft$^2$/hr) | Normalized Flux (LMH/psig) |
| --- | --- | --- |
| UF1 | 32 | 4.8 |
| DF | 56 | 2.4 |
| UF2 | 267 | 1.6 |

The protein pool was recovered by a series of steps. First the product is displaced from the membrane in a single pass mode using 0.2 L of DF buffer added to the retentate line. The product is filtered into a recovery tank through a 0.22 microns sterilizing-grade final filter. The pool in the recirculation tank was then pumped from the tank using the rotary lobe feed pump. Next, the residual protein solution is displaced from tank and feed line with a 5 psig nitrogen gas blow down. The final phase was a blow down of membrane unit, which now contains DF buffer from the initial product displacement. This phase also used the 5 psig nitrogen gas applied to the highest point on the retentate line.

If necessary, the recovered pool was diluted first to about 175 g 2H7/L using dilution buffer (30 mM sodium acetate, pH 5.3). Finally, the pool is diluted down to a target concentration of 150 g 2H7/L and conditioned into the final formulation of 30 mM sodium acetate, 7% trehalose, 0.03% polysorbate 20, pH 5, via a 7× conditioning buffer (30 mM sodium acetate, 49% trehalose, 0.21% polysorbate 20, pH 5.3). The volumes of the recovered pool, diluted pool, and conditioned pool were then analyzed for protein concentration. Table 17 presents the results.

TABLE 17

| | Volume (L) | Concentration (g/L) | Mass (g) | Yield or {Loss} (%) |
| --- | --- | --- | --- | --- |
| Q-Pool | 355.81 | 2.31 | 821.92 | 100.0 |
| Recovered Pool | 4.64 | 180.02 | 835.3 | 101.6 |
| Final Pool | 4.871 | 149.40 | 727.7 | 88.5 |

Note:
Yields include loss due to sampling. Recovered pool volume and concentration include addition of buffer displacement.

Post process, the membrane was regenerated using 0.1 N NaOH, 1 L/ft$^2$ single pass flush followed by 0.5 L/ft$^2$ total recirculation for 30 min. This was followed by 1 L/ft$^2$ PW flush. This was followed by a total recirculation of 0.5 L/ft$^2$ 1.4% Minncare® solution for 30 min. The system was again flushed with 1 L/ft$^2$ PW and finally recirculated for 15 min with 0.1 N NaOH and stored.

Example 11

High Concentration Formulation of rhuMAb anti-CD20 A pilot scale UF system was used to concentrate and formulate rhuMAb anti-CD20 (2H7) for use in a human phase I clinical study in a GMP manufacturing facility. Example 10 was repeated with the following exceptions.

The protein pool resulting from a preceding Q-Sepharose chromatography step was measured to be 3.729 g 2H7/L and had a volume of 262 L. The protein was in a solution of 6 mM HEPES free acid/19 mM HEPES sodium salt and 25 mM sodium acetate that had been pH adjusted to 5.3 with 0.5 M acetic acid. Just prior to the run, the temperature set point of this pool was set to 45° C. To begin the run the protein pool was transferred to the recirculation vessel through a 0.22 microns sterilizing grade filter to a level of about 40 L in the tank. In the vessel the pool was agitated via the top mounted impeller and the temperature was maintained at 40-50° C.

Figure 24:
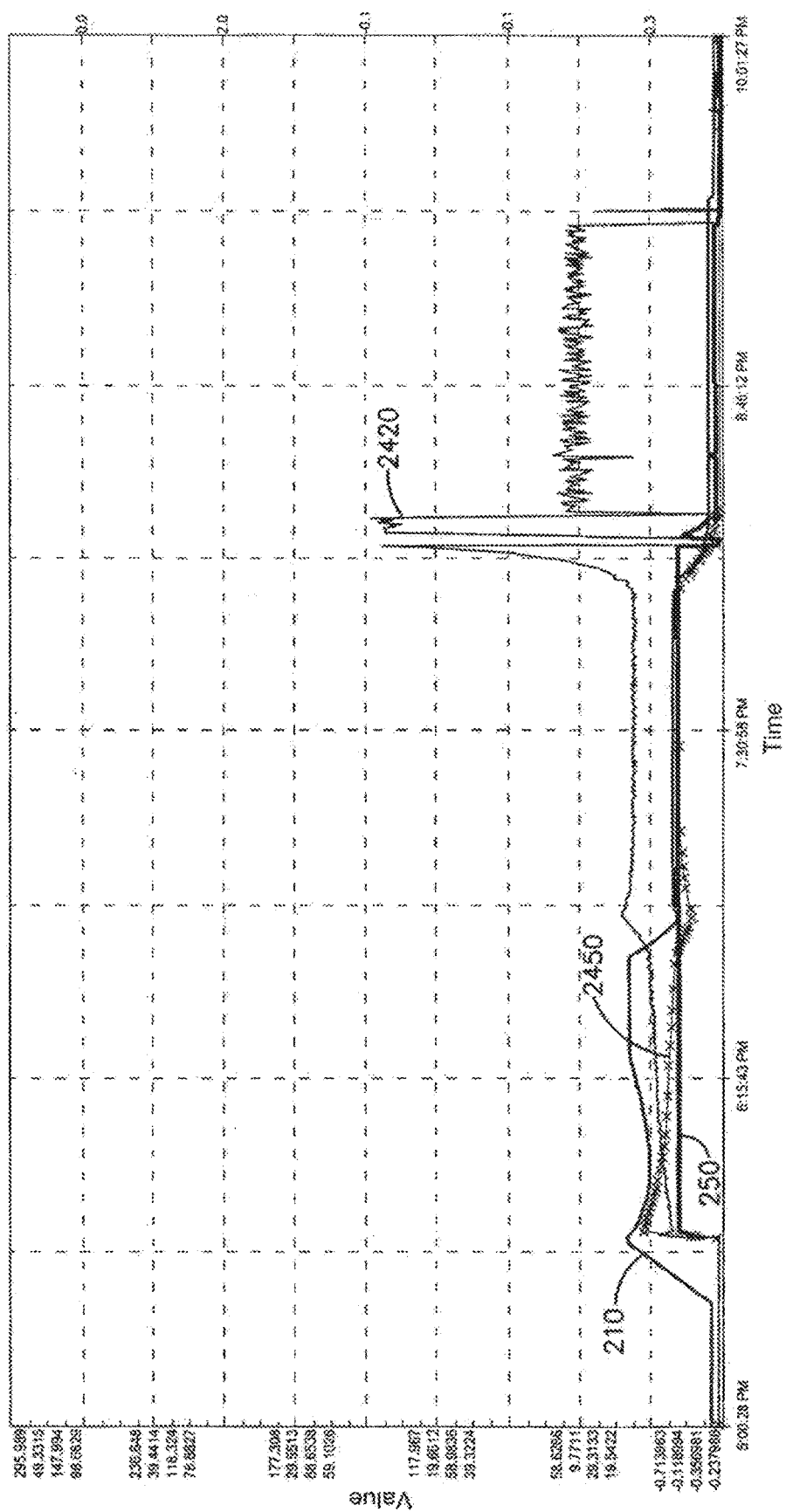

During the UF1 the pool was concentrated to about 50 g 2H7/L (about 20 L). FIG. 24 displays the value trends over time for recycle tank level (210) scaled from −0.713963 to 295.989, retentate dP (2420) scaled from −0.237899 to 98.6629, feed flow rate (250) scaled from −0.356981 to 147.994, and filtrate flow rate (2450) scaled from −0.118994 to 49.3315 during the process. The pool was then diafiltered with 10 diavolumes of diafiltration buffer. During diafiltration the temperature was maintained between 40 and 50° C. The diafiltration was performed at a constant volume, which was achieved by matching the flow rate of buffer being transferred into the recirculation tank to the flow rate of filtrate being removed from the system. At the end of the diafiltration, the pool was further concentrated in UF2 mode to a final concentration target set point of 190 g 2H7/L (5.25 L). Note in FIG. 24 the incorporation of constant dP to 40 psig control at the end of this phase. This phase was also performed at an elevated temperature set point of 45° C.+/−5° C. Next, a low pressure drop mixing was performed where the feed pump is controlled to maintain a 20 psig pressure drop across the feed channel. A sample was pulled and a density measurement was performed to confirm the concentration prior to recovery. The concentration of this sample was 194 g 2H7/L. Table 18 summarizes the throughput and flux results.

TABLE 18

| Process Phase | Normalized throughput (g/ft²/hr) | Normalized Flux (LMH/psig) |
|---|---|---|
| UF1 | 51 | 3.8 |
| DF | 46 | 2.2 |
| UF2 | 286 | 1.6 |

Just prior to product recovery, a 30 mL sample was pulled and submitted for detection and titer of bioburden. The results were negative (i.e., <0.13 CFU/mL), The protein pool was recovered by the series of steps of Example 10. The volumes of the recovered pool, diluted pool, and conditioned pool were then analyzed for protein concentration. Table 19 presents the results. The membrane was regenerated as in Example 10.

TABLE 19

|  | Volume (L) | Concentration (g/L) | Mass (g) | Yield or {Loss} (%) |
|---|---|---|---|---|
| Q-Pool | 262 | 3.72 | 977 | 100 |
| Recovered Pool | 5.0 | 174.0 | 863.0 | 88.3 |
| Diluted Pool | 5.421 | 149.6 | 811.0 | 83.0 |

Example 12

High Concentration Formulation of rhuMAb anti-CD20 GMP Example 11 was repeated with the following exceptions. The protein pool resulting from a preceding Q-Sepharose chromatography step was measured to be 5.106 g 2H7/L and had a volume of 196 L. The protein was in a solution of 6 mM HEPES free acid/19 mM HEPES sodium salt and 25 mM sodium acetate that had been pH adjusted to 5.3 with 0.5 M acetic acid. Just prior to the run, the temperature setpoint of this pool was set to 45° C. To begin the run the protein pool was transferred to the recirculation vessel through a 0.22 microns sterilizing grade filter to a level of about 40 L in the tank. In the vessel the pool was agitated via the top mounted impeller and the temperature was maintained at 40-50° C.

Figure 25:
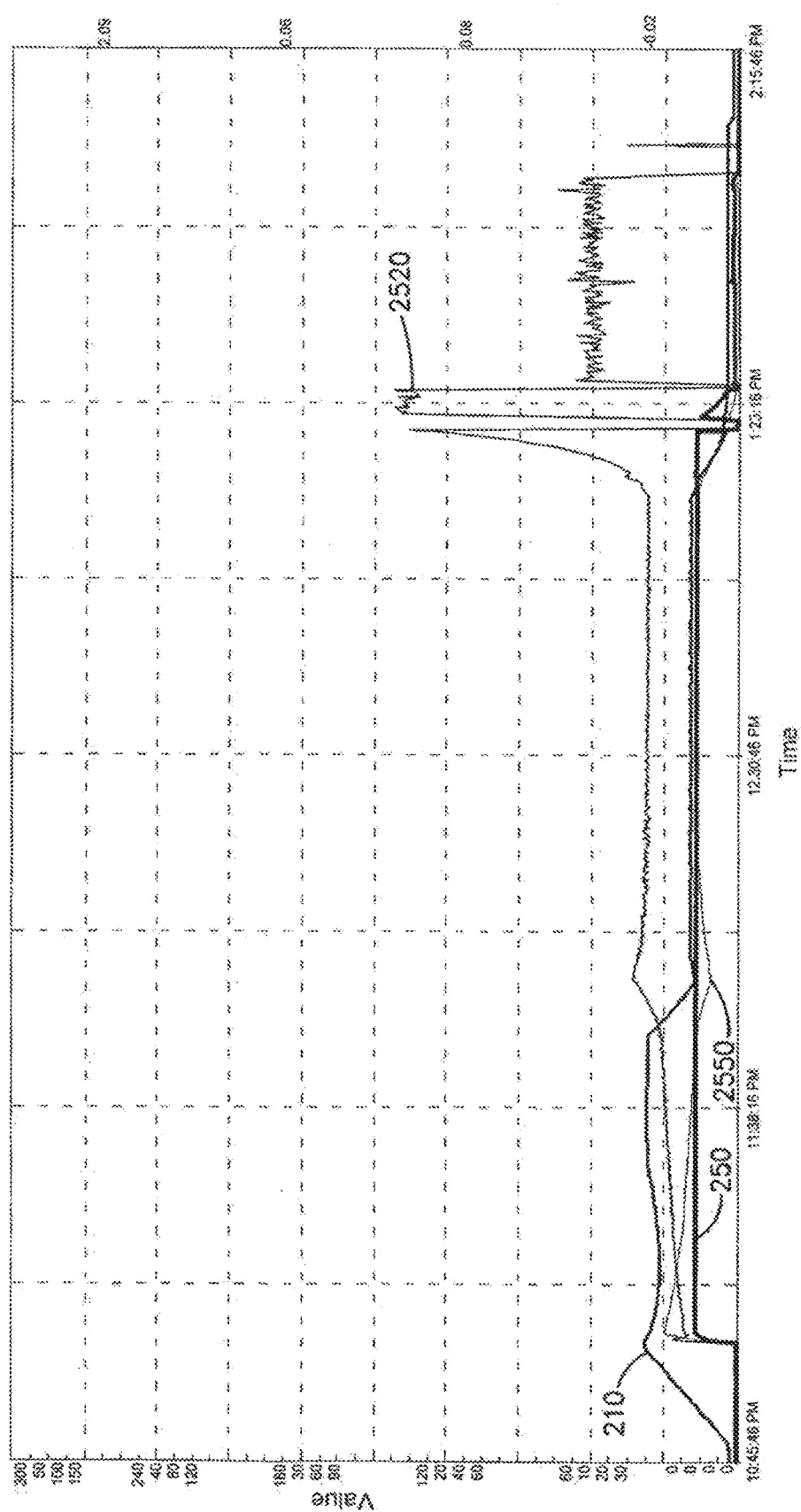

During the UF1 the pool was concentrated to about 50 g 2H7/L (about 2 L). FIG. 25 displays the value trends over time for recycle tank level (210) scaled from 0 to 300, retentate dP (2520) scaled from 0 to 100, feed flow rate (250) scaled from 0 to 150, and filtrate flow rate (2550) scaled from 0-50 during the process. The pool was diafiltered with 10 diavolumes (10x) of diafiltration buffer. During diafiltration the temperature was maintained between 40 and 50° C. The diafiltration was performed at a constant volume that was achieved by matching the flow rate of buffer being transferred into the recirculation tank to the flow rate of filtrate being removed from the system. At the end of the diafiltration, the pool was further concentrated in UF2 mode to a final concentration target setpoint of 190 g 2H7/L (5.26 L) again utilizing constant dP control at the very end of this phase (see FIG. 25). This phase was also performed at an elevated temperature set point of 45° C.+/−5° C. Next, a low pressure drop mixing was performed where the feed pump is controlled to maintain a 20 psig pressure drop across the feed channel. A sample was pulled and a density measurement was performed to confirm the concentration prior to recovery. The concentration of this sample was 191 g 2H7/L. Table 20 summarizes the throughput and flux results.

TABLE 20

| Process Phase | Normalized throughput (g/ft²/hr) | Normalized Flux (LMH/psig) |
|---|---|---|
| UF1 | 67 | 3.6 |
| DF | 47 | 2.1 |
| UF2 | 292 | 1.8 |

Just prior to product recovery, a 30 mL sample was pulled and submitted for detection and titer of bioburden. The results were negative (i.e., <0.13 CFU/mL). The protein pool was recovered by a series of steps as in Example 11. The volumes of the recovered pool, diluted pool, and conditioned pool were then analyzed for protein concentration. Table 21 presents the results. The membrane was regenerated as in Example 11.

TABLE 21

|  | Volume (L) | Concentration (g/L) | Mass (g) | Yield or {Loss} (%) |
|---|---|---|---|---|
| Q-Pool | 196 | 5.106 | 1000 | 100 |
| Recovered Pool | 4.9 | 187.1 | 918.0 | 91.8 |
| Diluted Pool | 6.075 | 150.9 | 916.9 | 91.7 |

All publications, patents, and patent documents are incorporated by reference herein in their entirety, as though individually incorporated by reference. The disclosure has been described with reference to various specific and preferred embodiments and techniques. However, it should be understood that many variations and modifications can be made while remaining within the spirit and scope of the disclosure.

The claimed invention is:

1. An ultrafiltration retentate diluted and conditioned to a final formulation comprising about 150 g/L (mg/ml) anti-IgE rhuMab E25 antibody, 0.02 M histidine, 0.2 M arginine-HCl, 0.04% polysorbate 20, pH 6, wherein the anti-IgE rhuMab E25 antibody is as described in U.S. Pat. No. 6,172,213, and wherein the ultrafiltration retentate is substantially free of soluble aggregates of the antibody.

2. An ultrafiltration retentate diluted and conditioned to a final formulation comprising about 150 g/L (mg/ml) anti-IgE rhuMab E25 antibody, 0.02 M histidine, 0.2 M arginine-HCl, 0.04% polysorbate 20, pH 6, wherein the ultrafiltration retentate was prepared at a temperature of about 45° C. plus or minus 5° C. and allowed to return to ambient temperature during dilution and conditioned, wherein the anti-IgE rhuMab E25 antibody is as described in U.S. Pat. No. 6,172,213, and wherein the ultrafiltration retentate is substantially free of soluble aggregates of the antibody.

3. The ultrafiltration retentate of claim 1, wherein the level of the aggregates in the ultrafiltration retentate is less than 5 weight %.

4. The ultrafiltration retentate of claim 1, wherein the level of the aggregates in the ultrafiltration retentate is less than 2 weight %.

5. The ultrafiltration retentate of claim 1, wherein the level of the aggregates in the ultrafiltration retentate is about 1 weight %.

6. The ultrafiltration retentate of claim 2, wherein the level of the aggregates in the ultrafiltration retentate is less than 5 weight %.

7. The ultrafiltration retentate of claim 2, wherein the level of the aggregates in the ultrafiltration retentate is less than 2 weight %.

8. The ultrafiltration retentate of claim 2, wherein the level of the aggregates in the ultrafiltration retentate is about 1 weight %.

\* \* \* \* \*